(12) United States Patent
Harada et al.

(10) Patent No.: US 7,612,253 B2
(45) Date of Patent: *Nov. 3, 2009

(54) METHODS OF MODULATING CYTOKININ RELATED PROCESSES IN A PLANT USING B3 DOMAIN PROTEINS

(75) Inventors: John Harada, Davis, CA (US); Sandra Stone, Fairfield, CA (US); Julie Pelletier, Davis, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/588,092

(22) Filed: Oct. 25, 2006

(65) Prior Publication Data

US 2007/0050867 A1    Mar. 1, 2007

Related U.S. Application Data

(63) Continuation of application No. 10/177,029, filed on Jun. 21, 2002, now Pat. No. 7,138,566.

(51) Int. Cl.
    *C12N 15/82*    (2006.01)
(52) U.S. Cl. .................. 800/278; 800/290; 800/287
(58) Field of Classification Search .................. None
    See application file for complete search history.

(56) References Cited

U.S. PATENT DOCUMENTS

| 6,124,525 | A  | * | 9/2000  | Botella .................. 623/1.15 |
| 6,294,714 | B1 | * | 9/2001  | Matsunaga et al. .......... 800/290 |
| 6,320,102 | B1 |   | 11/2001 | Harada et al. |
| 6,359,197 | B1 |   | 3/2002  | Amasino et al. |
| 7,138,566 | B2 | * | 11/2006 | Harada et al. ............... 800/290 |
| 2003/0226173 | A1 | * | 12/2003 | Ratcliffe et al. ............. 800/281 |
| 2005/0251883 | A1 | * | 11/2005 | Amasino et al. ............ 800/287 |

FOREIGN PATENT DOCUMENTS

| WO | WO 99/15667 A1 | 4/1999 |
| WO | WO 01/70777 A1 | 9/2001 |
| WO | WO 02/14520 A1 | 2/2002 |
| WO | WO 02/15675 A1 | 2/2002 |

OTHER PUBLICATIONS

Yang et al (2001, PNAS 98(20):11438-11443).*
Riechmann et al (2000, Current Opinion in Plant Biology 3:423-434).*
Bowie et al, Science 247:1306-1310, 1990.*
McConnell et al, Nature 411 (6838):709-713, 2001.*
Luerssen, Hartmut et al., "FUSCA3 encodes a protein with a conserved VP1/AB13-like B3 domain which is of functional importance for the regulation of seed maturation in *Arabidopsis thaliana*"; The Plant Journal, 1998, pp. 755-764, vol. 15(6).
Riechmann et al. (2000, Current Opinion in Plant Biology 3:423-434).
Roeckel et al. (1997, Transgenic Research 6(2):133-141).
Sa et al. (2002, Transgenic Research 11(3):269-278).
Sahoo, S.C. et al.; "Studies on the Effect of Growth Regulators on Seed Dormancy, Germination and Seedling Vigour of Coffee"; The Orissa Journal of Horticulture 1999, pp. 11-13, vol. 27(1).
Stone, Sandra L. et al.; "Leafy Cotyledon2 encodes a B3 domain transcription factor that induces embryo development"; PNAS, 2001, pp. 11806-11811, vol. 98(20).
Yang et al. (2001, PNAS 98(20):11438-11443).

* cited by examiner

*Primary Examiner*—Stuart F. Baum
(74) *Attorney, Agent, or Firm*—Townsend and Townsend and Crew LLP

(57) ABSTRACT

The present invention is directed to plant genetic engineering. In particular, it relates to methods of modulating cytokinin related processes in a plant and selecting a plant having a phenotype associated with an altered cytokinin-related process.

18 Claims, No Drawings

SEQUENCE LISTING

<160> NUMBER OF SEQ ID NOS: 34

<210> SEQ ID NO 1
<211> LENGTH: 6766
<212> TYPE: DNA
<213> ORGANISM: Arabidopsis thaliana
<220> FEATURE:
<223> OTHER INFORMATION: LEC2 genomic sequence

<400> SEQUENCE: 1

| | | | | | |
|---|---|---|---|---|---|
| atatatatat | atatatatat | atatatatat | ctttgagttc | atgattttt | tacaagaaga | 60 |
| ctatatagtt | ggtgatatgt | actctcacaa | catttttgtta | agaattctcc | aaaaacttat | 120 |
| atgtcatctt | acgaaaattg | ttaaacatca | aacagtcaca | tttgtaaaaa | gctaattaca | 180 |
| acaacattta | ttaacagtta | aaatataaat | ctcttaggta | gcccggatta | aaactcttaa | 240 |
| ttcaattgtt | acatatatat | tcgggagtag | tccaaatttt | cttctaatct | aatataataa | 300 |
| agtaatgcta | ttcttaagaa | caagttttga | gaaactgaca | tgtagatata | gaactctaaa | 360 |
| tatattatcc | taagaagcta | tggatttact | aatttcatcc | tatccctatg | tgaatcccta | 420 |
| aactcaacga | gagcattact | aagacatgat | catagaagca | tatatcatat | ttgaataaaa | 480 |
| ttacataaat | aattcaaaag | attatagagt | ttagaaagta | ttattttctt | tataaggttt | 540 |
| tgaaatctct | aaagaattct | tgaaaaatag | aaaacaaaaa | gtaaaagctt | gataattcta | 600 |

```
actattgacc caaaatatat taataggttc tcaaaaacat ttaggaacaa ataatgcaaa    660
tacaaaaatc ttatgggaca attatgtaat cttctaattt ttaaactggg aagacttttg    720
ttgggatgcg aacggtgtct atcgacatgt cgatcgacat tgattacttg atctgacacc    780
aaattcgttt tttcagcctt tattttccg tttggttcca aaatacttaa cgaactccaa    840
atatattcgc ataaataacc gaaaagattt taaaataac atagtaactc taaaaacaat    900
atctatatca taaataataa cggaaaataa tccatgatat atcaattata actcaaccaa    960
agccaacgaa caaaaaacat gaagcaaagc tacatatact actaatgata agtctaaatc   1020
gtcttcgaca tatctaacaa aaccaaaata tatatacttg gaaacaactt cttcacccgg   1080
acacaaattt ctcaaagcaa gtgtcaaaaa ctctacgata ataacaaaca gagtatatgt   1140
agctatgcaa tccaaggagc tttcctcttg tctaaaagtg tcataatggc ggaccggtcg   1200
caatcttatg tagctctacg ctacccctt tggctacgga aggtgcttga aattgataaa   1260 tacattcat tgttgtaatg attttctgta gtttgattgc ttttgtttcc tctttgtaat   1320
tgtgaacaag ttgttgttaa tatcatgaat cattcagaca gaaaaaaaa aataacaaac   1380 agagaaaaat cccaaaaaat aagaaaatat agatgacgct acatcactat atttcccta   1440 cctccttagt ctcgctagga gttacgagtc gtgcgcctct tccagtattt gccataatta   1500
actgagtggg atcttttgt ccatcaaccc atgcctcttc aatatttt actaatccac   1560 catttcctc cattgttat gatatatatg tttcaccaaa tatacctata caaaactata   1620
tttcaaactt ataacgaaca agaaaacgag ttttcaaaa tttcagagtt tatggccgag   1680
aataaacatg agctcggcgg ccgcggttta gaacaaaatt tgtgtccatc tcctcgccaa   1740
atgtaagttt ctgatagagc ataacattgg gttgggacga aaaggaaac caataagatg   1800 atagaaattg ctgggtaatt ggaggtgttc ttagggcacg agttgaacat gttaccaaac   1860
ctaattcatg gttagaaatt tggtgacagt caagcttata ttatctttga taactatgtt   1920
tctagttgtt tcattattag tatagaaaaa actttgtttt gtagagtgtt ctatgggtta   1980
tgatttcgaa aagaaaaaaa ttgtgagaca cctaataaaa ttatttcgac aaaaaaaata   2040
gcttgtataa aaaaatcaga ttttaattta tgtttgaaca aattccaata gttaaaaata   2100
attatttgtt ccgattaatc gagttttgca aaatatgcac aaaatctatc atcgtaccat   2160
ttctaagact atatatttgg ttatatattt tatgccgtgt tctgattcca aaaattttta   2220
gcgcatagta aattttctaa aaagcaaaat tttctcaaaa gtgtactaat gacaattaat   2280
tgagtttcta caaaataaga ataactattg actcgatttt cacaaaatta gtatgctaaa   2340
tatcacatta cttttaaaat taatggaat tgtcttttc aatattggat acgaataatt   2400
tttacactaa agttatttta ataaaataac cgtttattca aatatgtaa agacgacaaa   2460 aatatatatt aaatggaaaa acgactaact tagttttgc aaaataaaat ggatttgtcc   2520
ttttcaatgt ttgaatacaa aaaaaaatct ataataagtt tattatatta aaataacccg   2580
ttttttcaga atacgcaaaa acgacaaaaa atattaatt acaagaaat ttagtttata   2640 caaaaatatg aatggctatt aatggtgttt actctaaatt taattattat gcatttatgc   2700
taaatctttc taaaggtaca agattcgtt ttttcaatgt ttgaactgca tattaaggta   2760
tagatttgga ccttaacaga gttaatatat aaggaagaga gccaaggaac tccaaaataa   2820
aataaagagc cttctctctc tctctctgag aaaaaacaca tatagccaat gaccttctcg   2880
tggtcttctg tgccataaaa gccattatat acattcaaac acaatctggc gccacatata   2940
cacatgtact agtgtatgta tatgtcctaa cctctgtatt catatctctc tccttgtctg   3000
```

```
agtggtgcga tgggtatccc cataagctgc aaacattgaa ccatctgcaa cattttgact    3060
cgttttcttt tgtgttttc caacatctgt ctcttcttca ctcgctctct cctaatcaat     3120
ctccccaacg acctctcttt ttttttgttt cttcactcag atctctctcc ctctctctct    3180
ctctctccgg gaaaaatgga taacttctta cccttccct cttctaacgc aaactctgtc     3240
caagaactct ctatggatcc taacaacaat cgctcgcact tcacaacagt ccctacttat    3300
gatcatcatc aggctcagcc tcatcacttc ttgcctccgt tttcataccc ggtggagcag    3360
atggcggcgg tgatgaatcc tcagccggtt tacttatcgg agtgttatcc tcagatcccg    3420
gttacgcaaa ccgaagtga attcggttct ctggttggta atccttgttt gtggcaagag    3480
agaggtggtt ttcttgatcc gcgtatgacg aagatggcaa ggatcaacag gaaaaacgcc    3540
atgatgagat caagaaacaa ctctagccct aattctagtc caagtgagtt ggttgattca    3600
aagagacagc tgatgatgct taacttgaaa ataacgtgc agatctccga caagaaagat     3660
agctaccaac agtccacatt tgataacaag gtttggtttt ttttcgtccc aattttgaa    3720 tatgtacgat tttcttattt attttttggt tttcatgtta ttatatgaat atacaatt     3780 ttgggtgtat aaaactttat gatacaattt ttaattattt ttattttgtt ttggttgttg    3840
cttgtagaag cttagggttt tgtgtgagaa ggaattgaag aacagcgatg ttgggtcact    3900
cgggaggata gttctaccaa aggtatgtga attcttaaaa ttcttttaa tttctcgaac     3960 caatacttgg taaaaaattc tgtttgtttt catgattttt cttcttttc tgttattgta     4020 taatgataaa tgaaatgcat tgatgaaaat gataatcatc aatcacgtac gtcattgaaa    4080
atttaaaaca caatcccata aaaaaattct tagaagaata aagttatttt atgaggatta    4140
gacttccgtc atttttataca agagatttat ggaacacaag cacaaaaatc gttgcggcca   4200
catattatct cattattcaa tttcactgag ttttttcttgc acatttcatt ttactttcaa   4260 atttttacata atatgtttat ctaactgttt tctgtttaac caataaaaag ttttaagtct   4320
ttaaaataag tatccacacg aaaacaagat gaataagaaa catgagaaga aaatgtggac    4380
tgaagtaaag ttagtttaat caaattttgt ttggtttctg tacgaacttt tatgttttt    4440 attttttatt tatttagcaa gtagtatatg aattaattta atttttata gttttaaact     4500 tgattttttt aaagatagct tataattatt gaatatatgg aatgctactt cttccttcaa    4560
tgttgttatt tgtatttgtt aaatttgaaa ttgggttgaa gaaaatgaaa ggtcgtttat    4620
atgcctttcc taattaattg tccattgaat ggtttaccac tttacctcga aaaagtgaat    4680
aaataaaaat cattagggaa aaagattcta catatcttgg ggttttatca aactttaat    4740 caattttatt ttaatgatat cgttctttatt tttcttagca agacactaat acgtgaatca   4800
tggctttgga atgcagagag atgcagaagc aaatcttccg aagctatctg ataaagaagg    4860
aatcgttgta cagatgagag atgttttctc tatgcagtct tggtctttca aatacaagta    4920
aataattcgc tttctaatcc atttttcatt tcccaattaa cacaaccta atttttatgct   4980 caactgttag tccctttttg tgttaccggt tctcatactt agttttaaat tttgatttt     5040 ttttatcaat tgggaacagt attataatta gaagactaaa tgctcgtatt aatgacatag    5100
gttttggtcc aataacaaga gcagaatgta tgtcctcgag aacacaggta aattaaggag    5160
ctccaatatt atttcaaaag tacaaaatct tatgtaaaac tactttaaa taatatgat      5220 ttacctttc ctttttttt gtggtgataa ctaaggaga atttgtgaag caaaatggag       5280
ctgagatagg agacttttta acaatatacg aggacgaaaa caagaatctc gtgagctctc    5340
tatttacttc atttcctat ttaattttgt aaaaagacat gaaaaagtta aaaaaaatg      5400
```

-continued

```
attaattagt agtccaaaat tggaaattta aaaagtggtc tttgaattga gtttgttaag    5460
catccagaca aaagttttaa aacctttttc tgtcaatgat aactgttctt atatggtagg    5520
tattaataac ttgtgggcct aggggggaagt aaatactatg gagaaaattt tataataatt    5580
gaaatttggt taatttagag tttataatat ggtttgattt ggtttggtta ggacttatga    5640
cttatgtgtg tgtgtgtgat cgcttgttct tattacagta cttcgccatg aatggaaatt    5700
cgggaaaaca aaatgaagga agagaaaatg agtcgaggga aaggaaccac tacgaagagg    5760
caatgcttga ttacatacca agagacgaag aggaagcttc cattgcaatg ctcatcggaa    5820
atctaaacga tcactatccc atccctaacg atctcatgga cctcaccact gaccttcagc    5880
accatcaagc cacgtcctca atgacacctg aggatcacgc gtacgtgggt tcatccgatg    5940
atcaggtgag ctttaacgac tttgagtggt ggtgatatgg tggtggaagt tctcaagttc    6000
ataaccccct tatgaaaata gaccttaaga tatacaaaag agattaaaag aaaaaaaagt    6060
tagtatattt catcatatct ctcattgaag atgagattta tatctataat tgttttatat    6120
agtgttttta ttacttttct atcaatatat taaagtttta attaataaaa acgatcattt    6180
atcttcagta taattagttt ttaattacaa acaaaattat tctgagtttt atcacccaga    6240
agagattatc gacatcttgt tagcaaaaaa ccattaaaaa acacattagc acaattagag    6300
atatggactt tcgtctttcg ggatttccca aatagttgat attccgttac aaataatgga    6360
acgacatagg tgctggattg gttataacgt tcatagctaa cttgtaagaa ttgtcgaaaa    6420
cttttgaatt tgttaaaaaa gaaaatgaca attaaagtgt ttataatatg ttactagtgt    6480
gaaattatgt atcaattttt ttttgttaaa aaaatcattt tgtttctatt tagaaattta    6540
acgataactt gggaacactg ccttgcctta cacgcgatga agggtactat cgcctacaag    6600
ttttcttttt tcatttgttt tttggtcggc acctacaagt ttttctaaaa aggatgatgc    6660
atagtagtcg ccggtgggta atactaatag cttttctatc agacaaaaaa acatatgatt    6720 tttgtttttct tatttgctaa ttagaaaatc aagataagtt aagagg               6766
```

<210> SEQ ID NO 2
<211> LENGTH: 362
<212> TYPE: PRT
<213> ORGANISM: Arabidopsis thaliana
<220> FEATURE:
<223> OTHER INFORMATION: LEC2

<400> SEQUENCE: 2

```
Met Asp Asn Phe Leu Pro Phe Pro Ser Ser Asn Ala Asn Ser Val Gln
  1               5                  10                  15

Glu Leu Ser Met Asp Pro Asn Asn Arg Ser His Phe Thr Thr Val
             20                  25                  30

Pro Thr Tyr Asp His His Gln Ala Gln Pro His His Phe Leu Pro Pro
         35                  40                  45

Phe Ser Tyr Pro Val Glu Gln Met Ala Ala Val Met Asn Pro Gln Pro
     50                  55                  60

Val Tyr Leu Ser Glu Cys Tyr Pro Gln Ile Pro Val Thr Gln Thr Gly
 65                  70                  75                  80

Ser Glu Phe Gly Ser Leu Val Gly Asn Pro Cys Leu Trp Gln Glu Arg
                 85                  90                  95

Gly Gly Phe Leu Asp Pro Arg Met Thr Lys Met Ala Arg Ile Asn Arg
            100                 105                 110

Lys Asn Ala Met Met Arg Ser Arg Asn Asn Ser Ser Pro Asn Ser Ser
        115                 120                 125
```

```
Pro Ser Glu Leu Val Asp Ser Lys Arg Gln Leu Met Met Leu Asn Leu
    130                 135                 140

Lys Asn Asn Val Gln Ile Ser Asp Lys Lys Asp Ser Tyr Gln Gln Ser
145                 150                 155                 160

Thr Phe Asp Asn Lys Lys Leu Arg Val Leu Cys Glu Lys Glu Leu Lys
                165                 170                 175

Asn Ser Asp Val Gly Ser Leu Gly Arg Ile Val Leu Pro Lys Arg Asp
            180                 185                 190

Ala Glu Ala Asn Leu Pro Lys Leu Ser Asp Lys Glu Gly Ile Val Val
        195                 200                 205

Gln Met Arg Asp Val Phe Ser Met Gln Ser Trp Ser Phe Lys Tyr Lys
    210                 215                 220

Phe Trp Ser Asn Asn Lys Ser Arg Met Tyr Val Leu Glu Asn Thr Gly
225                 230                 235                 240

Glu Phe Val Lys Gln Asn Gly Ala Glu Ile Gly Asp Phe Leu Thr Ile
                245                 250                 255

Tyr Glu Asp Glu Ser Lys Asn Leu Tyr Phe Ala Met Asn Gly Asn Ser
            260                 265                 270

Gly Lys Gln Asn Glu Gly Arg Glu Asn Glu Ser Arg Glu Arg Asn His
        275                 280                 285

Tyr Glu Glu Ala Met Leu Asp Tyr Ile Pro Arg Asp Glu Glu Ala
    290                 295                 300

Ser Ile Ala Met Leu Ile Gly Asn Leu Asn Asp His Tyr Pro Ile Pro
305                 310                 315                 320

Asn Asp Leu Met Asp Leu Thr Thr Asp Leu Gln His Gln Ala Thr
                325                 330                 335

Ser Ser Met Thr Pro Glu Asp His Ala Tyr Val Gly Ser Asp Asp
            340                 345                 350

Gln Val Ser Phe Asn Asp Phe Glu Trp Trp
        355                 360

<210> SEQ ID NO 3
<211> LENGTH: 3195
<212> TYPE: DNA
<213> ORGANISM: Arabidopsis thaliana
<220> FEATURE:
<221> NAME/KEY: promoter
<222> LOCATION: (1)..(3195)
<223> OTHER INFORMATION: LEC2 5' promoter

<400> SEQUENCE: 3
atatatatat atatatatat atatatatat ctttgagttc atgattttt tacaagaaga    60 ctatatagtt ggtgatatgt actctcacaa cattttgtta agaattctcc aaaaacttat   120
atgtcatctt acgaaaattg ttaaacatca aacagtcaca tttgtaaaaa gctaattaca   180
acaacattta ttaacagtta aaatataaat ctcttaggta gcccggatta aaactcttaa   240
ttcaattgtt acatatatat tcgggagtag tccaaatttt cttctaatct aatataataa   300
agtaatgcta ttcttaagaa caagtttga gaaactgaca tgtagatata gaactctaaa   360
tatattatcc taagaagcta tggatttact aatttcatcc tatccctatg tgaatcccta   420
aactcaacga gagcattact aagacatgat catagaagca tatatcatat ttgaataaaa   480
ttacataaat aattcaaaag attatagagt ttagaaagta ttattttctt tataaggttt   540
tgaaatctct aaagaattct tgaaaaatag aaaacaaaaa gtaaagcttg ataattcta   600 actattgacc caaatatat taataggttc tcaaaaacat ttaggaacaa ataatgcaaa   660
```

-continued

```
tacaaaaatc ttatgggaca attatgtaat cttctaattt ttaaactggg aagacttttg      720
ttgggatgcg aacggtgtct atcgacatgt cgatcgacat tgattacttg atctgacacc      780
aaattcgttt tttcagcctt tattttccg tttggttcca aaatacttaa cgaactccaa       840
atatattcgc ataaataacc gaaaagattt ttaaaataac atagtaactc taaaaacaat      900
atctatatca taaataataa cggaaaataa tccatgatat atcaattata actcaaccaa      960
agccaacgaa caaaaaacat gaagcaaagc tacatatact actaatgata agtctaaatc     1020
gtcttcgaca tatctaacaa aaccaaaata tatatacttg gaaacaactt cttcacccgg     1080
acacaaattt ctcaaagcaa gtgtcaaaaa ctctacgata taacaaaca gagtatatgt      1140 agctatgcaa tccaaggagc tttcctcttg tctaaaagtg tcataatggc ggaccggtcg     1200
caatcttatg tagctctacg ctacccctt tggctacgga aggtgcttga aattgataaa      1260
tacattacat tgttgtaatg attttctgta gtttgattgc ttttgtttcc tctttgtaat     1320
tgtgaacaag ttgttgttaa tatcatgaat cattcagaca gaaaaaaaaa aataacaaac     1380
agagaaaaat cccaaaaaat aagaaaatat agatgacgct acatcactat atttccccta    1440
cctccttagt ctcgctagga gttacgagtc gtgcgcctct tccagtattt gccataatta    1500
actgagtggg atcttttgt ccatcaaccc atgcctcttc aatattttt actaatccac      1560 catttccttc cattgttatt gatatatatg tttcaccaaa tatacctata caaaactata    1620
tttcaaactt ataacgaaca agaaaacgag ttttccaaaa tttcagagtt tatggccgag    1680
aataaacatg agctcggcgg ccgcggttta gaacaaaatt tgtgtccatc tcctcgccaa    1740
atgtaagttt ctgatagagc ataacattgg gttgggacga aaaggaaac caataagatg    1800 atagaaattg ctgggtaatt ggaggtgttc ttagggcacg agttgaacat gttaccaaac    1860
ctaattcatg gttagaaatt tggtgacagt caagcttata ttatctttga taactatgtt    1920
tctagttgtt tcattattag tatagaaaaa actttgtttt gtagagtgtt ctatgggtta    1980
tgatttcgaa aagaaaaaaa ttgtgagaca cctaataaaa ttatttcgac aaaaaaaata    2040
gcttgtataa aaaaatcaga ttttaattta tgtttgaaca aattccaata gttaaaaata    2100
attatttgtt ccgattaatc gagttttgca aaatatgcac aaaatctatc atcgtaccat    2160
ttctaagact atatatttgg ttatatattt tatgccgtgt tctgattcca aaaattttta    2220
gcgcatagta aattttctaa aaagcaaaat tttctcaaaa gtgtactaat gacaattaat    2280
tgagtttcta caaaataaga ataactattg actcgatttt cacaaaatta gtatgctaaa    2340
tatcacatta cttttaaaat taaatggaat tgtcttttc aatattggat acgaataatt    2400
tttacactaa agttatttta ataaaataac cgtttattca aaatatgtaa agacgacaaa    2460
aatatatatt aaatggaaaa acgactaact tagttttgc aaaataaaat ggatttgtcc    2520
ttttcaatgt ttgaatacaa aaaaaatct ataataagtt tattatatta aaataaccg     2580 tttttcaga atacgcaaaa acgacaaaaa aatattaatt acaagaaat ttagttata      2640 caaaatatg aatggctatt aatggtgttt actctaaatt taattattat gcattatgc    2700 taaatctttc taaaggtaca aagattcgtt ttttcaatgt ttgaactgca tattaaggta    2760
tagatttgga ccttaacaga gttaatatat aaggaagaga gccaaggaac tccaaaataa    2820
aataaagagc cttctctctc tctctctgag aaaaacaca tatagccaat gaccttctcg    2880
tggtcttctg tgccataaaa gccattatat acattcaaac acaatctggc gccacatata    2940
cacatgtact agtgtatgta tatgtcctaa cctctgtatt catatctctc tccttgtctg    3000
agtggtgcga tgggtatccc cataagctgc aaacattgaa ccatctgcaa cattttgact    3060
```

```
cgttttcttt tgtgtttttc caacatctgt ctcttcttca ctcgctctct cctaatcaat    3120
ctccccaacg acctctcttt tttttgtttt cttcactcag atctctctcc ctctctctct    3180
ctctctccgg gaaaa                                                     3195
```

<210> SEQ ID NO 4
<211> LENGTH: 1000
<212> TYPE: DNA
<213> ORGANISM: Arabidopsis thaliana
<220> FEATURE:
<221> NAME/KEY: promoter
<222> LOCATION: (1)..(1000)
<223> OTHER INFORMATION: LEC2 3' promoter

<400> SEQUENCE: 4

```
aataaaaacg atcatttatc ttcagtataa ttagtttta attacaaaca aaattattct      60
gagttttatc acccagaaga gattatcgac atcttgttag caaaaaacca ttaaaaaaca    120
cattagcaca attagagata tggactttcg tctttcggga tttcccaaat agttgatatt    180
ccgttacaaa taatggaacg acataggtgc tggattggtt ataacgttca tagctaactt    240
gtaagaattg tcgaaaactt ttgaatttgt taaaaagaa aatgacaatt aaagtgttta    300
taatatgtta ctagtgtgaa attatgtatc aatttttttt tgttaaaaaa atcattttgt    360
ttctatttag aaatttaacg ataacttggg aacactgcct tgccttacac gcgatgaagg    420
gtactatcgc ctacaagttt tcttttttca tttgtttttt ggtcggcacc tacaagtttt    480
tctaaaaagg atgatgcata gtagtcgccg gtgggtaata ctaatagctt ttctatcaga    540
caaaaaaaca tatgattttt gttttcttat ttgctaatta gaaaatcaag ataagttaag    600
aggccttgat tccctaaacc ctagccctct aacgctagcc tagattctaa tccaagccca    660
aaactattac tagtataact ctgagtatat ccgagctctt ataactattg cccatactct    720
atttatagct agcccaacag aattactcaa tactccaaac ccaatagtct aaccctacct    780
gggatactac actgatcagt tagccctgac agaaaccagt tgacaaaaat accgaacctt    840
catagaactg aaaataatag agataaaagg ttcatgcaat acgtaggttt gatttacaat    900
ccgctattgt aattagtttt caatcgtttt tgtgaaaatg aaacatgtaa gtttatcaaa    960
ttcaacctct tatcaaaacc tatttaattt gaatagatac                         1000
```

<210> SEQ ID NO 5
<211> LENGTH: 1296
<212> TYPE: DNA
<213> ORGANISM: Arabidopsis thaliana
<220> FEATURE:
<223> OTHER INFORMATION: LEC2 cDNA

<400> SEQUENCE: 5

```
atggataact tcttacccct tccctcttct aacgcaaaact ctgtccaaga actctctatg     60
gatcctaaca caatcgctc gcacttcaca acagtcccta cttatgatca tcatcaggct    120
cagcctcatc acttcttgcc tccgttttca tacccggtgg agcagatggc ggcggtgatg    180
aatcctcagc cggtttactt atcggagtgt atcctcaga tcccggttac gcaaaccgga    240
agtgaattcg gttctctggt tggtaatcct tgtttgtggc aagagagagg tggttttctt    300
gatccgcgta tgacgaagat ggcaaggatc aacaggaaaa acgccatgat gagatcaaga    360
aacaactcta gccctaattc tagtccaagt gagttggttg attcaaagag acagctgatg    420
atgcttaact tgaaaataa cgtgcagatc tccgacaaga aagatagcta ccaacagtcc    480
acatttgata acaagaagct tagggttttg tgtgagaagg aattgaagaa cagcgatgtt    540
```

-continued

```
gggtcactcg ggaggatagt tctaccaaag agagatgcag aagcaaatct tccgaagcta      600
tctgataaag aaggaatcgt tgtacagatg agagatgttt tctctatgca gtcttggtct      660
ttcaaataca agttttggtc caataacaag agcagaatgt atgtcctcga aacacagga       720 gaatttgtga agcaaaatgg agctgagata ggagactttt aacaatata cgaggacgaa       780 agcaagaatc tctacttcgc catgaatgga aattcgggaa acaaaatga aggaagagaa       840 aatgagtcga gggaaaggaa ccactacgaa gaggcaatgc ttgattacat accaagagac      900
gaagaggaag cttccattgc aatgctcatc ggaaatctaa cgatcacta tcccatccct       960 aacgatctca tggacctcac cactgacctt cagcaccatc aagccacgtc tcaatgaca      1020 cctgaggatc acgcgtacgt gggttcatcc gatgatcagg tgagctttaa cgactttgag    1080
tggtggtgat atggtggtgg aagttctcaa gttcataacc cccttatgaa aatagacctt    1140
aagatataca aaagagatta aagaaaaaa agttagtat atttcatcat atctctcatt      1200
gaagatgaga tttatatcta taattgtttt atatagtgtt tttattactt ttctatcaat    1260
atattaaagt tttaattaaa aaaaaaaaaa aaaaaa                              1296

<210> SEQ ID NO 6
<211> LENGTH: 2968
<212> TYPE: DNA
<213> ORGANISM: Arabidopsis thaliana
<220> FEATURE:
<223> OTHER INFORMATION: LEC2 gene from translation start site to
      polyadenylation site

<400> SEQUENCE: 6
atggataact tcttacccttt tccctcttct aacgcaaaact ctgtccaaga actctctatg     60
gatcctaaca caatcgctc gcacttcaca acagtcccta cttatgatca tcatcaggct     120
cagcctcatc acttcttgcc tccgttttca tacccggtgg agcagatggc ggcggtgatg    180
aatcctcagc cggtttactt atcggagtgt atcctcaga tcccggttac gcaaaccgga     240
agtgaattcg gttctctggt tggtaatcct tgtttgtggc aagagagagg tggttttctt    300
gatccgcgta tgacgaagat ggcaaggatc aacaggaaaa acgccatgat gagatcaaga    360
aacaactcta gccctaattc tagtccaagt gagttggttg attcaaagag acagctgatg    420
atgcttaact tgaaaaataa cgtgcagatc tccgacaaga agatagcta ccaacagtcc     480 acatttgata caaggtttg gtttttttc gtcccaattt ttgaatatgt acgattttct      540 tatttattt ttggttttca tgttattata tgaatatata caattttggg tgtataaaac     600
tttatgatac aatttttaat tatttttatt ttgttttggt tgttgcttgt agaagcttag    660
ggttttgtgt gagaaggaat tgaagaacag cgatgtgggg tcactcggga ggatagttct    720
accaaaggta tgtgaattct taaaattctt tttaatttct cgaaccaata cttggtaaaa    780
aattctgttt gttttcatga ttttttcttct ttttctgtta ttgtataatg ataaatgaaa    840
tgcattgatg aaaatgataa tcatcaatca cgtacgtcat tgaaaattta aaacacaatc    900
ccataaaaaa attcttagaa gaataaagtt attttatgag gattagactt ccgtcatttt    960
atacaagaga tttatggaac acaagcacaa aaatcgttgc ggccacatat tatctcatta   1020
ttcaatttca ctgagttttt cttgcacatt tcatttttact ttcaaatttt acataatatg   1080
tttatctaac tgttttctgt ttaaccaata aaaagtttta agtctttaaa ataagtatcc   1140
acacgaaaac aagatgaata agaaacatga gaagaaaatg tggactgaag taaagttagt   1200
ttaatcaaat tttgtttggt ttctgtacga actttttatgt ttttgatttt ttatttattt   1260
```

```
agcaagtagt atatgaatta atttaatttt ttatagtttt aaacttgatt ttttttaaaga    1320 tagcttataa ttattgaata tatggaatgc tacttcttcc ttcaatgttg ttatttgtat    1380
ttgttaaatt tgaaatttggg ttgaagaaaa tgaaaggtcg tttatatgcc tttcctaatt   1440
aattgtccat tgaatggttt accactttac ctcgaaaaag tgaataaata aaaatcatta    1500
gggaaaaaga ttctacatat cttggggttt tatcaaactt ttaatcaatt ttattttaat    1560
gatatcgttc ttatttttct tagcaagaca ctaaacgtg aatcatggct ttggaatgca     1620
gagagatgca gaagcaaatc ttccgaagct atctgataaa gaaggaatcg ttgtacagat    1680
gagagatgtt ttctctatgc agtcttggtc tttcaaatac aagtaaataa ttcgctttct    1740
aatccatttt tcatttccca attaacacaa ccttaatttt atgctcaact gttagtccct    1800
ttttgtgtta ccggttctca tacttagttt taaattttga tttttttta tcaattggga    1860 acagtattat aattagaaga ctaaatgctc gtattaatga cataggtttt ggtccaataa    1920
caagagcaga atgtatgtcc tcgagaacac aggtaaatta aggagctcca atattatttc    1980
aaaagtacaa atcttatgt aaaactactt ttaaataaat atgatttacc ttttcctttt     2040
tttttgtggt gataactaaa ggagaatttg tgaagcaaaa tggagctgag ataggagact    2100
ttttaacaat atacgaggac gaaagcaaga atctcgtgag ctctctattt acttcatttc    2160
cctatttaat tttgtaaaaa gacatgaaaa agttaaaaaa aaatgattaa ttagtagtcc    2220
aaaattggaa atttaaaaag tggtctttga attgagtttg ttaagcatcc agacaaaagt    2280
tttaaaacct ttttctgtca atgataactg ttccttatatg gtaggtatta ataacttgtg   2340
ggcctagggg gaagtaaata ctatggagaa aattttataa taattgaaat ttggttaatt    2400
tagagtttat aatatggttt gatttggttt ggttaggact tatgacttat gtgtgtgtgt    2460
gtgatcgctt gttcttatta cagtacttcg ccatgaatgg aaattcggga aaacaaaatg    2520
aaggaagaga aaatgagtcg agggaaagga accactacga agaggcaatg cttgattaca    2580
taccaagaga cgaagaggaa gcttccattg caatgctcat cggaaatcta aacgatcact    2640
atcccatccc taacgatctc atggacctca ccactgacct tcagcaccat caagccacgt    2700
cctcaatgac acctgaggat cacgcgtacg tgggttcatc cgatgatcag gtgagcttta    2760
acgactttga gtggtggtga tatggtggtg gaagttctca agttcataac cccttatga    2820 aaatagacct taagatatac aaaagagatt aaaagaaaaa aagttagta tatttcatca    2880 tatctctcat tgaagatgag atttatatct ataattgttt tatatagtgt ttttattact    2940
tttctatcaa tatattaaag tttttaatt                                       2968
```

```
<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence:LEC2 B3
      domain

<400> SEQUENCE: 7
```

Gln Gln Ser Thr Phe Asp Asn Lys Lys Leu Arg Val Leu Cys Glu Lys
  1               5                  10                  15

Glu Leu Lys Asn Ser Asp Val Gly Ser Leu Gly Arg Ile Val Leu Pro
             20                  25                  30

Lys Arg Asp Ala Glu Ala Asn Leu Pro Lys Leu Ser Asp Lys Glu Gly
         35                  40                  45

```
Ile Val Val Gln Met Arg Asp Val Phe Ser Met Gln Ser Trp Ser Phe
 50                  55                  60
Lys Tyr Lys Phe Trp Ser Asn Asn Lys Ser Arg Met Tyr Val Leu Glu
 65                  70                  75                  80
Asn Thr Gly Glu Phe Val Lys Gln Asn Gly Ala Glu Ile Gly Asp Phe
                 85                  90                  95
Leu Thr Ile Tyr Glu Asp Glu Ser Lys Asn Leu Tyr Phe Ala Met Asn
            100                 105                 110
Gly Asn Ser
        115

<210> SEQ ID NO 8
<211> LENGTH: 1256
<212> TYPE: DNA
<213> ORGANISM: Arabidopsis thaliana
<220> FEATURE:
<223> OTHER INFORMATION: Arabidopsis ecotype Col FUS3 (FUSCA3) cDNA

<400> SEQUENCE: 8
cacaaaccac agtctctctt tctctctcta tctatcttct ctttctctct ctatctctat    60
cactgaaacc caaagagatc caccatttgt tcttttttcc ttcacacaga gaactgtttt   120
cttccacact tccttttac taggcagtgt taaccaattg agagagaaaa atgatggttg   180
atgaaaatgt ggaaaccaag gcctctactt tagtggcaag tgttgatcat gggtttggat   240
ccgggtcggg tcatgatcat catgggttat cggcgtctgt gcctcttctt ggtgttaact   300
ggaagaagag aaggatgcct agacagagac gatcttcttc ttccttttaac cttctctctt   360 tccctcctcc tatgcctcct atttcccacg tgccaactcc tctccccgca cgtaaaattg   420
acccaagaaa gctaagattc ctcttccaaa aggaactcaa gaacagtgac gtcagctctc   480
tccgacgtat gatactcccg aagaaagccg cggaggctca cttgccggca cttgaatgca   540
aggaagggat tcctataaga atggaagatt tggacggttt tcacgtttgg accttcaagt   600
ataggtactg gccaaacaac aatagcagaa tgtacgtgct agaaaacaca ggcgattttg   660
tgaatgctca tggtctgcag ctaggtgact tcatcatggt ttaccagat ctctactcaa    720 acaattacgt tatacaagca agaaaagcat cggaagaaga agaagtagac gtaatcaatc   780
ttgaagaaga cgacgtttac acaaacttaa caaggatcga aaacactgtg gttaacgatc   840
ttctcctcca agattttaat catcacaaca acaacaacaa caacaacagc aacagcaaca   900
gcaacaaatg ttcttactat tatccagtca tagatgatgt caccacaaac acagagtctt   960 tttgtctacga cacgacggct cttacctcca acgatactcc tctcgattt ttgggtggac    1020 atacgacgac tactaataat tattactcca agttcggaac attcgatggt ttgggctccg   1080
ttgagaatat ctctctcgat gacttctact agataatcaa tcgatgggct catggtattc   1140
ttgatggtga tcagctattt aatatcctta taatatatat aagaattaaa tgcaattgc    1200 atatattatta tcaagtgttg aatataacat tacaaaaact aaaaaaaaa aaaaaa        1256

<210> SEQ ID NO 9
<211> LENGTH: 313
<212> TYPE: PRT
<213> ORGANISM: Arabidopsis thaliana
<220> FEATURE:
<223> OTHER INFORMATION: Arabidopsis ecotype Col FUS3 (FUSCA3)
```

```
<400> SEQUENCE: 9

Met Met Val Asp Glu Asn Val Glu Thr Lys Ala Ser Thr Leu Val Ala
1               5                   10                  15

Ser Val Asp His Gly Phe Gly Ser Gly Ser Gly His Asp His His Gly
            20                  25                  30

Leu Ser Ala Ser Val Pro Leu Leu Gly Val Asn Trp Lys Lys Arg Arg
        35                  40                  45

Met Pro Arg Gln Arg Arg Ser Ser Ser Phe Asn Leu Leu Ser Phe
    50                  55                  60

Pro Pro Pro Met Pro Pro Ile Ser His Val Pro Thr Pro Leu Pro Ala
65              70                  75                  80

Arg Lys Ile Asp Pro Arg Lys Leu Arg Phe Leu Phe Gln Lys Glu Leu
                85                  90                  95

Lys Asn Ser Asp Val Ser Ser Leu Arg Arg Met Ile Leu Pro Lys Lys
                100                 105                 110

Ala Ala Glu Ala His Leu Pro Ala Leu Glu Cys Lys Glu Gly Ile Pro
            115                 120                 125

Ile Arg Met Glu Asp Leu Asp Gly Phe His Val Trp Thr Phe Lys Tyr
130                 135                 140

Arg Tyr Trp Pro Asn Asn Ser Arg Met Tyr Val Leu Glu Asn Thr
145                 150                 155                 160

Gly Asp Phe Val Asn Ala His Gly Leu Gln Leu Gly Asp Phe Ile Met
                165                 170                 175

Val Tyr Gln Asp Leu Tyr Ser Asn Asn Tyr Val Ile Gln Ala Arg Lys
            180                 185                 190

Ala Ser Glu Glu Glu Val Asp Val Ile Asn Leu Glu Glu Asp Asp
        195                 200                 205

Val Tyr Thr Asn Leu Thr Arg Ile Glu Asn Thr Val Val Asn Asp Leu
210                 215                 220

Leu Leu Gln Asp Phe Asn His His Asn Asn Asn Asn Asn Asn Ser
225                 230                 235                 240

Asn Ser Asn Ser Asn Lys Cys Ser Tyr Tyr Tyr Pro Val Ile Asp Asp
                245                 250                 255

Val Thr Thr Asn Thr Glu Ser Phe Val Tyr Asp Thr Thr Ala Leu Thr
            260                 265                 270

Ser Asn Asp Thr Pro Leu Asp Phe Leu Gly Gly His Thr Thr Thr Thr
        275                 280                 285

Asn Asn Tyr Tyr Ser Lys Phe Gly Thr Phe Asp Gly Leu Gly Ser Val
    290                 295                 300

Glu Asn Ile Ser Leu Asp Asp Phe Tyr
305                 310

<210> SEQ ID NO 10
<211> LENGTH: 1106
<212> TYPE: DNA
<213> ORGANISM: Arabidopsis thaliana
<220> FEATURE:
<223> OTHER INFORMATION: Arabidopsis ecotype Ler FUS3 (FUSCA3) cDNA

<400> SEQUENCE: 10
cacaaaccac agtctctctt tctctctcta tctatcttct ctttctctct ctatctctat        60
cactgaaacc caaagagatc caccatttgt tcttttttcc ttcacacaga gaactgtttt       120
cttccacact tccttttac taggcagtgt taaccaattg agagagaaaa atgatggttg        180
atgaaaatgt ggaaaccaat gcctctactt tagtggcaag tgttgatcat gggtttggat       240
```

-continued

```
ccgggtcggg tcatgatcat catgggttat cggcgtctgt gcctcttctt ggtgttaact      300
ggaagaagag aaggatgcct agacagagac gatcttcttc ttcctttaac cttctctctt      360
tccctcctcc tatgcctcct atttcccacg tgacaactcc tctccccgca cgtaaaattg      420
acccaagaaa gctaagattc ctcttccaaa aggaactcaa gaacagtgac gtcagctccc      480
tccgacgtat gatactcccg aagaaagccg cggaggctca cttgccggca cttgaatgca      540
aggaagggat tcctataaga atggaagatt tggacggttt tcacgtttgg accttcaagt      600
ataggtactg gccaaacaac aatagcagaa tgtacgtgct agaaaacaca ggcgattttg      660
tgaatgctca tggtctgcag ctaggtgact tcatcatggt ttaccaagat ctctactcaa      720
acaattacgt tatacaagca agaaaagcat cggaagaaga agaagtagac gtaatcaatc      780
ttgaagaaga cgacgtttac acaaacttaa caaggatcga aaacactgtg gttaacgatc      840
ttctcctcca agattttaat catcacaaca acaacaacaa caacagcaac agcaacaaca      900
aatgttctta ctattatcca gtcatagatg atgtcaccac aaacacagag tcttttgtct      960
acgacacgac ggctcttacc tccaacgata ctcctctcga ttttttgggt ggacatacga     1020
cgactactaa taattattac tccaagttcg gaacattcga tggtttgggc tccgttgaga     1080
atatctctct cgatgacttc tactag                                          1106
```

<210> SEQ ID NO 11
<211> LENGTH: 933
<212> TYPE: DNA
<213> ORGANISM: Arabidopsis thaliana
<220> FEATURE:
<223> OTHER INFORMATION: Arabidopsis ecotype Ler FUS3 (FUSCA3) gene

<400> SEQUENCE: 11

```
atggttgatg aaaatgtgga aaccaatgcc tctactttag tggcaagtgt tgatcatggg       60
tttggatccg ggtcgggtca tgatcatcat gggttatcgg cgtctgtgcc tcttcttggt      120
gttaactgga agaagagaag gatgcctaga cagagacgat cttcttcttc ctttaacctt      180
ctctctttcc ctcctcctat gcctcctatt tcccacgtga caactcctct ccccgcacgt      240
aaaattgacc caagaaagct aagattcctc ttccaaaagg aactcaagaa cagtgacgtc      300
agctccctcc gacgtatgat actcccgaag aaagccgcgg aggctcactt gccggcactt      360
gaatgcaagg aagggattcc tataagaatg gaagatttgg acggttttca cgtttggacc      420
ttcaagtata ggtactggcc aaacaacaat agcagaatgt acgtgctaga aaacacaggc      480
gattttgtga atgctcatgg tctgcagcta ggtgacttca tcatggttta ccaagatctc      540
tactcaaaca attacgttat acaagcaaga aaagcatcgg aagaagaaga agtagacgta      600
atcaatcttg aagaagacga cgtttacaca aacttaacaa ggatcgaaaa cactgtggtt      660
aacgatcttc tcctccaaga ttttaatcat cacaacaaca acaacaacaa caacagcaac      720
agcaacaaat gttcttacta ttatccagtc atagatgatg tcaccacaaa cacagagtct      780
tttgtctacg acacgacggc tcttacctcc aacgatactc ctctcgattt tttgggtgga      840
catacgacga ctactaataa ttattactcc aagttcggaa cattcgatgg tttgggctcc      900
gttgagaata tctctctcga tgacttctac tag                                  933
```

<210> SEQ ID NO 12
<211> LENGTH: 310
<212> TYPE: PRT
<213> ORGANISM: Arabidopsis thaliana
<220> FEATURE:
<223> OTHER INFORMATION: Arabidopsis ecotype Ler FUS3 (FUSCA3)

<400> SEQUENCE: 12

Met Val Asp Glu Asn Val Glu Thr Asn Ala Ser Thr Leu Val Ala Ser
1               5                   10                  15

Val Asp His Gly Phe Gly Ser Gly Ser Gly His Asp His His Gly Leu
            20                  25                  30

Ser Ala Ser Val Pro Leu Leu Gly Val Asn Trp Lys Lys Arg Arg Met
        35                  40                  45

Pro Arg Gln Arg Arg Ser Ser Ser Phe Asn Leu Leu Ser Phe Pro
    50                  55                  60

Pro Pro Met Pro Pro Ile Ser His Val Thr Thr Pro Leu Pro Ala Arg
65                  70                  75                  80

Lys Ile Asp Pro Arg Lys Leu Arg Phe Leu Phe Gln Lys Glu Leu Lys
                85                  90                  95

Asn Ser Asp Val Ser Ser Leu Arg Arg Met Ile Leu Pro Lys Lys Ala
            100                 105                 110

Ala Glu Ala His Leu Pro Ala Leu Glu Cys Lys Glu Gly Ile Pro Ile
        115                 120                 125

Arg Met Glu Asp Leu Asp Gly Phe His Val Trp Thr Phe Lys Tyr Arg
    130                 135                 140

Tyr Trp Pro Asn Asn Asn Ser Arg Met Tyr Val Leu Glu Asn Thr Gly
145                 150                 155                 160

Asp Phe Val Asn Ala His Gly Leu Gln Leu Gly Asp Phe Ile Met Val
                165                 170                 175

Tyr Gln Asp Leu Tyr Ser Asn Asn Tyr Val Ile Gln Ala Arg Lys Ala
            180                 185                 190

Ser Glu Glu Glu Val Asp Val Ile Asn Leu Glu Glu Asp Asp Val
        195                 200                 205

Tyr Thr Asn Leu Thr Arg Ile Glu Asn Thr Val Val Asn Asp Leu Leu
    210                 215                 220

Leu Gln Asp Phe Asn His His Asn Asn Asn Asn Asn Asn Ser Asn
225                 230                 235                 240

Ser Asn Lys Cys Ser Tyr Tyr Tyr Pro Val Ile Asp Asp Val Thr Thr
                245                 250                 255

Asn Thr Glu Ser Phe Val Tyr Asp Thr Thr Ala Leu Thr Ser Asn Asp
            260                 265                 270

Thr Pro Leu Asp Phe Leu Gly Gly His Thr Thr Thr Asn Asn Tyr
    275                 280                 285

Tyr Ser Lys Phe Gly Thr Phe Asp Gly Leu Gly Ser Val Glu Asn Ile
290                 295                 300

Ser Leu Asp Asp Phe Tyr
305                 310

<210> SEQ ID NO 13
<211> LENGTH: 930
<212> TYPE: DNA
<213> ORGANISM: Arabidopsis thaliana
<220> FEATURE:
<223> OTHER INFORMATION: Arabidopsis ecotype Ws-0 FUS3 (FUSCA3) gene

<400> SEQUENCE: 13
atggttgatg aaaatgtgga aaccaaggcc tctactttag tggcaagtgt tgatcatggg      60
tttggatccg ggtcgggtca tgatcatcat gggttatcgg cgtctgtgcc tcttcttggt     120

-continued

```
gttaactgga agaagagaag gatgcctaga cagagacgat cttcttcttc ctttaacctt     180
ctctctttcc ctcctcctat gcctcctatt tcccacgtgc caactcctct ccccgcacgt     240
aaaattgacc caagaaagct aagattcctc ttccaaaagg aactcaagaa cagtgacgtc     300
agctccctcc gacgtatgat actcccgaag aaagccgcgg aggctcactt gccggcactt     360
gaatgcaagg aagggattcc tataagaatg gaagatttgg acggttttca cgtttggacc     420
ttcaagtata ggtactggcc aaacaacaat agcagaatgt acgtgctaga aaacacaggc     480
gattttgtga atgctcatgg tctgcagcta ggtgacttca tcatggttta ccaagatctc     540
tactcaaaca attacgttat acaagcaaga aaagcatcgg aagaagaaga agtagacgta     600
atcaatcttg aagaagacga cgtttacaca aacttaacaa ggatcgaaaa cactgtggtt     660
aacgatcttc tcctccaaga ttttaatcat cacaacaaca acaacaacaa cagcaacagc     720
aacaaatgtt cttactatta tccagtcata gatgatgtca ccacaaacac agagtcttt     780 gtctacgaca cgacggctct tacctccaac gatactcctc tcgattttt gggtggacat     840 acgacgacta ctaataatta ttactccaag ttcggaacat tcgatggttt gggctccgtt     900
gagaatatct ctctcgatga cttctactag                                      930
```

<210> SEQ ID NO 14
<211> LENGTH: 309
<212> TYPE: PRT
<213> ORGANISM: Arabidopsis thaliana
<220> FEATURE:
<223> OTHER INFORMATION: Arabidopsis ecotype Ws-0 FUS3 (FUSCA3)

<400> SEQUENCE: 14

```
Met Val Asp Glu Asn Val Glu Thr Lys Ala Ser Thr Leu Val Ala Ser
 1               5                  10                  15

Val Asp His Gly Phe Gly Ser Gly Ser Gly His Asp His His Gly Leu
                20                  25                  30

Ser Ala Ser Val Pro Leu Leu Gly Val Asn Trp Lys Lys Arg Arg Met
            35                  40                  45

Pro Arg Gln Arg Arg Ser Ser Ser Ser Phe Asn Leu Leu Ser Phe Pro
        50                  55                  60

Pro Pro Met Pro Pro Ile Ser His Val Pro Thr Pro Leu Pro Ala Arg
65                  70                  75                  80

Lys Ile Asp Pro Arg Lys Leu Arg Phe Leu Phe Gln Lys Glu Leu Lys
                85                  90                  95

Asn Ser Asp Val Ser Ser Leu Arg Arg Met Ile Leu Pro Lys Lys Ala
            100                 105                 110

Ala Glu Ala His Leu Pro Ala Leu Glu Cys Lys Glu Gly Ile Pro Ile
        115                 120                 125

Arg Met Glu Asp Leu Asp Gly Phe His Val Trp Thr Phe Lys Tyr Arg
    130                 135                 140

Tyr Trp Pro Asn Asn Asn Ser Arg Met Tyr Val Leu Glu Asn Thr Gly
145                 150                 155                 160

Asp Phe Val Asn Ala His Gly Leu Gln Leu Gly Asp Phe Ile Met Val
                165                 170                 175

Tyr Gln Asp Leu Tyr Ser Asn Asn Tyr Val Ile Gln Ala Arg Lys Ala
            180                 185                 190

Ser Glu Glu Glu Glu Val Asp Val Ile Asn Leu Glu Glu Asp Asp Val
        195                 200                 205

Tyr Thr Asn Leu Thr Arg Ile Glu Asn Thr Val Val Asn Asp Leu Leu
    210                 215                 220
```

```
Leu Gln Asp Phe Asn His His Asn Asn Asn Asn Asn Ser Asn Ser
225                 230                 235                 240

Asn Lys Cys Ser Tyr Tyr Tyr Pro Val Ile Asp Asp Val Thr Thr Asn
                245                 250                 255

Thr Glu Ser Phe Val Tyr Asp Thr Thr Ala Leu Thr Ser Asn Asp Thr
            260                 265                 270

Pro Leu Asp Phe Leu Gly Gly His Thr Thr Thr Asn Asn Tyr Tyr
        275                 280                 285

Ser Lys Phe Gly Thr Phe Asp Gly Leu Gly Ser Val Glu Asn Ile Ser
        290                 295                 300

Leu Asp Asp Phe Tyr
305

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence:FUS3
      (FUSCA3) B3 domain

<400> SEQUENCE: 15

Pro Ala Arg Lys Ile Asp Pro Arg Lys Leu Arg Phe Leu Phe Gln Lys
1               5                   10                  15

Glu Leu Lys Asn Ser Asp Val Ser Leu Arg Arg Met Ile Leu Pro
            20                  25                  30

Lys Lys Ala Ala Glu Ala His Leu Pro Ala Leu Glu Cys Lys Glu Gly
        35                  40                  45

Ile Pro Ile Arg Met Glu Asp Leu Asp Gly Phe His Val Trp Thr Phe
    50                  55                  60

Lys Tyr Arg Tyr Trp Pro Asn Asn Asn Ser Arg Met Tyr Val Leu Glu
65                  70                  75                  80

Asn Thr Gly Asp Phe Val Asn Ala His Gly Leu Gln Leu Gly Asp Phe
                85                  90                  95

Ile Met Val Tyr Gln Asp Leu Tyr Ser Asn Asn Tyr Val Ile Gln Ala
            100                 105                 110

Arg Lys Ala
        115

<210> SEQ ID NO 16
<211> LENGTH: 78
<212> TYPE: PRT
<213> ORGANISM: Artificial Sequence
<220> FEATURE:
<223> OTHER INFORMATION: Description of Artificial Sequence:LEC2/FUS3
      family B3 domain consensus sequence
<220> FEATURE:
<221> NAME/KEY: MOD_RES
<222> LOCATION: (1)..(78)
<223> OTHER INFORMATION: Xaa = any amino acid

<400> SEQUENCE: 16

Leu Xaa Xaa Xaa Asp Xaa Xaa Xaa Xaa Arg Xaa Xaa Leu Pro Lys
1               5                   10                  15

Xaa Xaa Ala Glu Xaa Xaa Xaa Pro Xaa Xaa Xaa Xaa Xaa Gly Xaa
            20                  25                  30

Xaa Xaa Xaa Xaa Xaa Asp Xaa Xaa Xaa Xaa Xaa Trp Xaa Xaa Xaa
        35                  40                  45
```

```
Xaa Xaa Xaa Trp Xaa Xaa Xaa Xaa Arg Xaa Tyr Xaa Leu Glu Xaa
         50                  55                  60

Xaa Xaa Xaa Xaa Xaa Xaa Xaa Xaa Xaa Xaa Xaa Gly Asp
 65                  70                  75

<210> SEQ ID NO 17
<211> LENGTH: 99
<212> TYPE: PRT
<213> ORGANISM: Artificial Sequence
<220> FEATURE:
<223> OTHER INFORMATION: Description of Artificial Sequence:LEC2, FUS3,
      ABI3 and VP1 B3 domain consensus sequence
<220> FEATURE:
<221> NAME/KEY: MOD_RES
<222> LOCATION: (1)..(99)
<223> OTHER INFORMATION: Xaa = any amino acid

<400> SEQUENCE: 17

Leu Arg Xaa Leu Xaa Xaa Lys Xaa Leu Lys Xaa Ser Asp Val Xaa Xaa
 1               5                  10                  15

Leu Xaa Arg Xaa Xaa Leu Pro Lys Xaa Xaa Ala Glu Xaa Xaa Leu Pro
             20                  25                  30

Xaa Leu Xaa Xaa Xaa Xaa Gly Ile Xaa Xaa Xaa Met Xaa Asp Xaa Xaa
         35                  40                  45

Xaa Xaa Xaa Xaa Trp Xaa Xaa Xaa Tyr Xaa Xaa Trp Xaa Asn Asn Xaa
         50                  55                  60

Ser Arg Met Tyr Xaa Leu Glu Asn Thr Gly Xaa Phe Val Xaa Xaa Xaa
 65                  70                  75                  80

Xaa Xaa Xaa Xaa Gly Asp Phe Xaa Xaa Xaa Tyr Xaa Asp Xaa Xaa Xaa
                 85                  90                  95

Xaa Xaa Tyr

<210> SEQ ID NO 18
<211> LENGTH: 103
<212> TYPE: PRT
<213> ORGANISM: Artificial Sequence
<220> FEATURE:
<223> OTHER INFORMATION: Description of Artificial Sequence:LEC2 and
      FUS3 B3 domain consensus sequence
<220> FEATURE:
<221> NAME/KEY: MOD_RES
<222> LOCATION: (1)..(103)
<223> OTHER INFORMATION: Xaa = any amino acid

<400> SEQUENCE: 18

Asp Xaa Xaa Lys Leu Arg Xaa Leu Xaa Xaa Lys Glu Leu Lys Asn Ser
 1               5                  10                  15

Asp Val Xaa Ser Leu Xaa Arg Xaa Xaa Leu Pro Lys Xaa Xaa Ala Glu
             20                  25                  30

Ala Xaa Leu Pro Xaa Leu Xaa Xaa Lys Glu Gly Ile Xaa Xaa Xaa Met
         35                  40                  45

Xaa Asp Xaa Xaa Xaa Xaa Xaa Trp Xaa Phe Lys Tyr Xaa Xaa Trp
         50                  55                  60

Xaa Asn Asn Xaa Ser Arg Met Tyr Val Leu Glu Asn Thr Gly Xaa Phe
 65                  70                  75                  80

Val Xaa Xaa Xaa Gly Xaa Xaa Gly Asp Phe Xaa Xaa Xaa Tyr Xaa
                 85                  90                  95

Asp Xaa Xaa Xaa Asn Xaa Tyr
            100
```

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:LEC2 genomic
      region amplification primer D2F

<400> SEQUENCE: 19
tttcagaata cgcaaaaacg ac                                                 22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:LEC2 genomic
      region amplification primer D2R

<400> SEQUENCE: 20
aactatcctc ccgagtgacc                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:LEC2 genomic
      region amplification primer Ef

<400> SEQUENCE: 21
agatggcaag gatcaacagg                                                    20

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:LEC2 genomic
      region amplification primer BlastR

<400> SEQUENCE: 22
cttgctttcg tcctcgtata ttg                                                23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:LEC2 genomic
      region amplification primer F2F

<400> SEQUENCE: 23
tttgtgaagc aaaatggagc                                                    20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:LEC2 genomic
      region amplification primer Stop

<400> SEQUENCE: 24
cggatgaacc cacgtacg                                                      18
```

```
<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence:LEC2 cDNA
      amplification primer

<400> SEQUENCE: 25
aaatggataa cttcttaccc tttcc                                           25

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:LEC2 cDNA
      amplification primer

<400> SEQUENCE: 26
cggatgaacc cacgtacg                                                   18

<210> SEQ ID NO 27
<211> LENGTH: 114
<212> TYPE: PRT
<213> ORGANISM: Artificial Sequence
<220> FEATURE:
<223> OTHER INFORMATION: Description of Artificial Sequence:Arabidopsis
      thaliana ABI3 B3 domain

<400> SEQUENCE: 27

Gln Gly Trp Lys Pro Glu Lys Asn Leu Arg Phe Leu Leu Gln Lys Val
  1               5                  10                  15

Leu Lys Gln Ser Asp Val Gly Asn Leu Gly Arg Ile Val Leu Pro Lys
             20                  25                  30

Lys Glu Ala Glu Thr His Leu Pro Glu Leu Glu Ala Arg Asp Gly Ile
         35                  40                  45

Ser Leu Ala Met Glu Asp Ile Gly Thr Ser Arg Val Trp Asn Met Arg
     50                  55                  60

Tyr Arg Phe Trp Pro Asn Asn Lys Ser Arg Met Tyr Leu Leu Glu Asn
 65                  70                  75                  80

Thr Gly Asp Phe Val Lys Thr Asn Gly Leu Gln Glu Gly Asp Phe Ile
                 85                  90                  95

Val Ile Tyr Ser Asp Val Lys Cys Gly Lys Tyr Leu Ile Arg Gly Val
            100                 105                 110

Lys Val

<210> SEQ ID NO 28
<211> LENGTH: 114
<212> TYPE: PRT
<213> ORGANISM: Artificial Sequence
<220> FEATURE:
<223> OTHER INFORMATION: Description of Artificial Sequence:Zea mays
      VIVIPAROUS1 (VP1) B3 domain

<400> SEQUENCE: 28

Gln Gly Ala Lys Ala Asp Lys Asn Leu Arg Phe Leu Leu Gln Lys Val
  1               5                  10                  15

Leu Lys Gln Ser Asp Val Gly Ser Leu Gly Arg Ile Val Leu Pro Lys
             20                  25                  30

Lys Glu Ala Glu Val His Leu Pro Glu Leu Lys Thr Arg Asp Gly Ile
         35                  40                  45
```

```
Ser Ile Pro Met Glu Asp Ile Gly Thr Ser Arg Val Trp Asn Met Arg
        50                  55                  60

Tyr Arg Phe Trp Pro Asn Asn Lys Ser Arg Met Tyr Leu Leu Glu Asn
 65                  70                  75                  80

Thr Gly Glu Phe Val Arg Ser Asn Glu Leu Gln Glu Gly Asp Phe Ile
                85                  90                  95

Val Ile Tyr Ser Asp Val Lys Ser Gly Lys Tyr Leu Ile Arg Gly Val
            100                 105                 110

Lys Val

<210> SEQ ID NO 29
<211> LENGTH: 109
<212> TYPE: PRT
<213> ORGANISM: Artificial Sequence
<220> FEATURE:
<223> OTHER INFORMATION: Description of Artificial Sequence:Arabidopsis
      thaliana AT2G30470 B3 domain

<400> SEQUENCE: 29

Asn Leu Asn Leu Asn Ile Val Pro Leu Phe Glu Lys Thr Leu Ser Ala
 1               5                  10                  15

Ser Asp Ala Gly Arg Ile Gly Arg Leu Val Leu Pro Lys Ala Cys Ala
                20                  25                  30

Glu Ala Tyr Phe Pro Pro Ile Ser Gln Ser Gly Ile Pro Leu Lys
            35                  40                  45

Ile Gln Asp Val Arg Gly Arg Glu Trp Thr Phe Gln Phe Arg Tyr Trp
        50                  55                  60

Pro Asn Asn Asn Ser Arg Met Tyr Val Leu Glu Gly Val Thr Pro Cys
 65                  70                  75                  80

Ile Gln Ser Met Met Leu Gln Ala Gly Asp Thr Val Thr Phe Ser Arg
                85                  90                  95

Val Asp Pro Gly Gly Lys Leu Ile Met Gly Ser Arg Lys
            100                 105

<210> SEQ ID NO 30
<211> LENGTH: 114
<212> TYPE: PRT
<213> ORGANISM: Artificial Sequence
<220> FEATURE:
<223> OTHER INFORMATION: Description of Artificial Sequence:Arabidopsis
      thaliana AT4G32010 B3 domain

<400> SEQUENCE: 30

Thr Val Tyr Phe Pro Ser Ser Asn Ser Lys Ile Ile Pro Leu Phe Glu
 1               5                  10                  15

Lys Val Leu Ser Ala Ser Asp Ala Gly Arg Ile Gly Arg Leu Val Leu
                20                  25                  30

Pro Lys Ala Cys Ala Glu Ala Tyr Phe Pro Pro Ile Ser Leu Pro Glu
            35                  40                  45

Gly Leu Pro Leu Lys Ile Gln Asp Ile Lys Gly Lys Glu Trp Val Phe
        50                  55                  60

Gln Phe Arg Phe Trp Pro Asn Asn Asn Ser Arg Met Tyr Val Leu Glu
 65                  70                  75                  80

Gly Val Thr Pro Cys Ile Gln Ser Met Gln Leu Gln Ala Gly Asp Thr
                85                  90                  95

Val Thr Phe Ser Arg Thr Glu Pro Glu Gly Lys Leu Val Met Gly Tyr
            100                 105                 110

Arg Lys
```

```
<210> SEQ ID NO 31
<211> LENGTH: 105
<212> TYPE: PRT
<213> ORGANISM: Artificial Sequence
<220> FEATURE:
<223> OTHER INFORMATION: Description of Artificial Sequence:Arabidopsis
      thaliana AT4G21550 B3 domain

<400> SEQUENCE: 31

Ile Asp Thr Thr Leu Glu Tyr Asn Phe Lys Ile Leu Ser Ala Thr Asp
  1               5                  10                  15

Thr Gly Lys Arg Leu Val Leu Pro Lys Lys Tyr Ala Glu Ala Phe Leu
             20                  25                  30

Pro Gln Leu Ser His Thr Lys Gly Val Pro Leu Thr Val Gln Asp Pro
         35                  40                  45

Met Gly Lys Glu Trp Arg Phe Gln Phe Arg Phe Trp Pro Ser Ser Lys
     50                  55                  60

Gly Arg Ile Tyr Val Leu Glu Gly Val Thr Pro Phe Ile Gln Thr Leu
 65                  70                  75                  80

Gln Leu Gln Ala Gly Asp Thr Val Ile Phe Ser Arg Leu Asp Pro Glu
                 85                  90                  95

Arg Lys Leu Ile Leu Gly Phe Arg Lys
            100                 105

<210> SEQ ID NO 32
<211> LENGTH: 114
<212> TYPE: PRT
<213> ORGANISM: Artificial Sequence
<220> FEATURE:
<223> OTHER INFORMATION: Description of Artificial Sequence:Arabodopsis
      thaliana FUS3 (FUSCA3) B3 domain

<400> SEQUENCE: 32

Pro Ala Arg Lys Ile Asp Pro Arg Lys Leu Arg Phe Leu Phe Gln Lys
  1               5                  10                  15

Glu Leu Lys Asn Ser Asp Val Ser Ser Leu Arg Arg Met Ile Leu Pro
             20                  25                  30

Lys Lys Ala Ala Glu Ala His Leu Pro Ala Leu Glu Cys Lys Glu Gly
         35                  40                  45

Ile Pro Ile Arg Met Glu Asp Leu Asp Gly Phe His Val Trp Thr Phe
     50                  55                  60

Lys Tyr Arg Tyr Trp Pro Asn Asn Asn Ser Arg Met Tyr Val Leu Glu
 65                  70                  75                  80

Asn Thr Gly Asp Phe Val Asn Ala His Gly Leu Gln Leu Gly Asp Phe
                 85                  90                  95

Ile Met Val Tyr Gln Asp Leu Tyr Ser Asn Asn Tyr Val Ile Gln Ala
            100                 105                 110

Arg Lys

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence:Zea mays
      ABI3 B3 domain
```

```
-continued

<400> SEQUENCE: 33

Gln Gly Trp Lys Pro Glu Lys Asn Leu Arg Phe Leu Leu Gln Lys Val
1               5                   10                  15

Leu Lys Gln Ser Asp Val Gly Asn Leu Gly Arg Ile Val Leu Pro Lys
                20                  25                  30

Lys Glu Ala Glu Thr His Leu Pro Glu Leu Glu Ala Arg Asp Gly Ile
            35                  40                  45

Ser Leu Ala Met Glu Asp Ile Gly Thr Ser Arg Val Trp Asn Met Arg
        50                  55                  60

Tyr Arg Phe Trp Pro Asn Asn Lys Ser Arg Met Tyr Leu Leu Glu Asn
65                  70                  75                  80

Thr Gly Asp Phe Val Lys Thr Asn Gly Leu Gln Glu Gly Asp Phe Ile
                85                  90                  95

Val Ile Tyr Ser Asp Val Lys Cys Gly Lys Tyr Leu Ile Arg Gly Val
                100                 105                 110

Lys

<210> SEQ ID NO 34
<211> LENGTH: 116
<212> TYPE: PRT
<213> ORGANISM: Artificial Sequence
<220> FEATURE:
<223> OTHER INFORMATION: Description of Artificial Sequence:B3 domain
      consensus sequence
<220> FEATURE:
<221> NAME/KEY: MOD_RES
<222> LOCATION: (1)..(116)
<223> OTHER INFORMATION: Xaa = any amino acid

<400> SEQUENCE: 34

Xaa Xaa Xaa Xaa Xaa Xaa Xaa Xaa Xaa Xaa Xaa Xaa Xaa Xaa Xaa Xaa
1               5                   10                  15

Xaa Xaa Leu Xaa Xaa Xaa Asp Xaa Xaa Xaa Xaa Xaa Arg Xaa Xaa Leu
                20                  25                  30

Pro Lys Xaa Xaa Ala Glu Xaa Xaa Xaa Pro Xaa Xaa Xaa Xaa Xaa Xaa
            35                  40                  45

Gly Xaa Xaa Xaa Xaa Xaa Xaa Asp Xaa Xaa Xaa Xaa Xaa Xaa Trp Xaa
        50                  55                  60

Xaa Xaa Xaa Xaa Trp Xaa Xaa Xaa Xaa Xaa Arg Xaa Tyr Xaa Leu
65                  70                  75                  80

Glu Xaa Xaa Xaa Xaa Xaa Xaa Xaa Xaa Xaa Xaa Xaa Xaa Gly Asp
            85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa
        115
```

METHODS OF MODULATING CYTOKININ RELATED PROCESSES IN A PLANT USING B3 DOMAIN PROTEINS

CROSS REFERENCE TO RELATED APPLICATION

This application is a continuation of application Ser. No. 10/177,029 filed Jun. 21, 2002, the full disclosure of which is incorporated herein by reference.

FIELD OF THE INVENTION

The present invention is directed to plant genetic engineering. In particular, it relates to methods of modulating cytokinin related processes in a plant and selecting a plant having a phenotype associated with an altered cytokinin-related process.

BACKGROUND OF THE INVENTION

Cytokinins are a well-known class of plant growth hormones active in promoting cell division, cell growth and differentiation, and other physiological processes. In particular, cytokinins are active in processes regulating disease resistance, stress tolerance, drought tolerance, resistance to lodging, delayed senescence, apical dominance, and assimilate partitioning in a plant, Werner et al., *Proc. Natl. Acad. Sci*, 98(18)10487-10492 (2001), Haberer et al., *Plant Physiol.*, 128, pp. 354-362 (2002).

Senescence, which constitutes the final phase of development in plants, is a critical stage of the plant life cycle. It is part of the aging process that typically occurs before cell death and is characterized by changes in cell structure, metabolism and gene expression that effect a decline in the activities of plants. Inhibiting senescence in a plant has been identified as a way to prolong the active life-span of a plant. Certain hormones associated with senescence, e.g., cytokinin, when present in increased levels in plants, have been demonstrated to delay senescence and prolong plant activity.

It has been previously demonstrated that plants with altered senescence patterns have leaves that retain high levels of chlorophyll throughout seed and flower development. Tobacco plants with altered leaf senescence patterns have enhanced yield of biomass and flower, see U.S. Pat. No. 5,689,042.

Because of the importance of plants for food production, there is a continuous and substantial effort to improve plants, e.g., create plants with increased disease resistance phenotypes, increased stress and drought tolerant phenotypes, increased resistance to lodging phenotypes, delayed senescence phenotypes, apical dominance phenotypes, and assimilate partitioning phenotypes. Plants with improved phenotypes are better able to meet the demands of food production. Accordingly, there is a need to create plants with improved phenotypes. This invention addresses this and other needs.

BRIEF SUMMARY OF THE INVENTION

It has been discovered that the modulation, e.g., overexpression or underexpression, in a plant, of a B3 domain protein will affect cytokinin related processes in the plant. Accordingly, the present invention provides methods of modulating cytokinin related processes in a plant. The methods of modulating a cytokinin related process in a plant comprise the following steps: (1) introducing into the plant a construct comprising a plant promoter operably linked to a polynucleotide wherein the polynucleotide encodes a B3 domain protein comprising an amino acid sequence as displayed in SEQ ID NO:16, and (2) selecting a plant having a phenotype associated with an altered cytokinin related process. In one embodiment of the present invention, the B3 domain protein comprises an amino acid sequence as displayed in SEQ ID NO:18. In a second embodiment, the B3 domain protein is SEQ ID NO:2. In a third embodiment, the B3 domain protein is SEQ ID NO:9, SEQ ID NO:12 or SEQ ID NO:14.

A plant promoter is used in the methods of the present invention. In one aspect of the present invention, the plant promoter is a senescence inducible promoter. In another aspect, the plant promoter is a constitutive promoter, a tissue specific promoter, or a floral specific promoter. The promoter may preferentially direct expression in ovules, pistils, anthers, fruits, seed coats, vascular tissues, provascular tissues, or apical meristems.

In one aspect of the present invention, the cytokinin related process is senescence, the phenotype selected for is delayed senescence of a plant structure, and the selecting step comprises selecting a plant with delayed senescence of a vegetative plant structure or a reproductive plant structure. In one embodiment of the present invention, the vegetative structure is a leaf, stem or root. In a second embodiment, the reproductive structure is a seed, embryo, ovule, flower, pistil, anther or fruit. In a third embodiment, the selecting step comprises selecting a plant with larger plant parts as compared to a wild type plant, such as selecting a plant with larger seeds, larger ovules, or larger embryos as compared to a wild type plant. In a fourth embodiment, the selecting step comprises selecting a plant with an increased number of plant parts as compared to a wild type plant, such as selecting a plant with an increased number of seeds, an increased number of flowers, an increased number of fruits, or an increased number of stems as compared to a wild type plant. In a fifth embodiment, the selecting step comprises selecting a plant with ovule development in the absence of fertilization.

In another aspect of the present invention, the selecting step comprises selecting a plant with decreased internode elongation, smaller leaves, smaller fruits or a smaller size as compared to a wild type plant.

In another aspect of the present invention, the plant promoter is operably linked to the polynucleotide in an antisense orientation. In yet another aspect of the present invention, the construct is introduced into the plant by a sexual cross.

Definitions

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase and do not alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous.

The phrase "host cell" refers to a cell from any organism. Preferred host cells are derived from plants, bacteria, yeast, fungi, insects or other animals. Methods for introducing polynucleotide sequences into various types of host cells are well known in the art.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

A nucleic acid or polynucleotide encoding a B3 domain protein is a nucleic acid sequence comprising (or consisting of) a coding region of about 50 to about 6800 nucleotides, sometimes from about 100 to about 3000 nucleotides and sometimes from about 300 to about 1300 nucleotides which encodes a B3 domain of about 115 amino acid residues, sometimes of about 105 to 125 amino acid residues, and sometimes of about 90 to about 140 amino acid residues.

A "B3 domain protein" or "B3 domain polypeptide" is a protein comprising a B3 domain. B3 domain proteins can be, e.g., sequences of about 100 to about 1000, sometimes 200 to 450 amino acid residues. A B3 domain is a sequence of about 90 to about 140, sometimes of about 105 to 125, and preferably 115 amino acid residues. The B3 domain is a DNA binding region well-known and characterized in the art, see Stone et al., *Proc. Natl. Acad. Sci.,* 98:20 11806-11811 (2001), Giraudat et al., *Plant Cell,* 4, 1251-1261 (1992), Luerben et al., *Plant J.,* 15, 755-764 (1998), Kagaya et al., *Nucleic Acids Res.* 27, 470-478 (1999), McCarty et al., *Cell,* 66, 895-906, Ulmasov et al., *Science,* 76, 1865-1868. Examples of proteins with B3 domains include GenBank Accession Nos: AAD20695, ARF10, CAB43843, AAF08561, ARF6, ARF8, ARF7, BIPOSTO, AAF82232, AC025813, MP/IAA24/ARF5, ARF3/ETTIN, ARF4, ARF1, BAB10162, AAG12520, AAD20164, CAB71113, ARF9, AAF79263, AAG27097, AAD39615, AAF79371, AAF79686, AAB63625, AAD26965, AAC34233, CAB71904, AAF26476, AAC62776, BAB08947, AAF00671, RAV1, BAA95760, RAV2, AB13, FUS3, LEC2, AAB63089, CAA16588, CAA18719, AAD20409, BAB03184, AAC69145, AAD30572, BAB02078, BAB09917, AAF29400. Exemplary embodiments of B3 domains include a B3 domain identical or substantially identical to the B3 domain displayed in SEQ ID NO:7, SEQ ID NO:15, SEQ ID NO:16, SEQ ID NO:17 and SEQ ID NO:18.

A "LEC2 polynucleotide" is a nucleic acid sequence comprising (or consisting of) a coding region of about 50 to about 6800 nucleotides, sometimes from about 100 to about 3000 nucleotides and sometimes from about 300 to about 1300 nucleotides, which hybridizes to SEQ ID NO:1 under stringent conditions (as defined below), or which encodes a LEC2 polypeptide or fragment of at least 15 amino acids thereof (see U.S. application Ser. No. 09/527,058). LEC2 polynucleotides can also be identified by their ability to hybridize under low stringency conditions (e.g., Tm ~40° C.) to nucleic acid probes having a the sequence of SEQ ID NO:1. SEQ ID NO:1, SEQ ID NO:5 (the LEC2 cDNA) and SEQ ID NO:6 are examples of LEC2 polynucleotides.

A "LEC2 polypeptide" or "LEC2 protein" is a B3 domain protein. A LEC2 polypeptide has a sequence of about 50 to about 400, sometimes 100 to 150, and preferably 363 amino acid residues encoded by a LEC2 polynucleotide. LEC2 polypeptides are plant transcription factors characterized by the presence of a B3 domain. For instance, amino acid residues 158 to 272 represent the B3 domain of the polypeptide shown in SEQ ID NO:2. The B3 domain is known in the art and is shared by other transcription factors including VIVIPAROUS1 (VP1) ((McCarty, et al. (1989) *Plant Cell* 1:523-532), AUXIN RESPONSE FACTOR 1 (ARF1) (Ulmasov, T. et al. (1997) *Science* 276:1865-1868), FUSCA3 (Luerben, H., et al. (1998) *Plant J.* 15:755-764) and ABI3 (Giraudat, J., et al. (1992) *Plant Cell* 4, 1251-1261). The B3 domains of FUS3 (Reidt, W. et al. (2000) *Plant J.* 21:401-408), VP1 (Suzuki, M. et al. (1997) *Plant Cell* 9:799-807) and ARF1 (Ulmasov, T., et al., supra) have been shown to be DNA binding domains. LEC2 and FUS3 both activate the promoter of a storage protein gene in transient expression assays, indicating that the B3 domain of LEC2 is a DNA binding domain and is shown in SEQ ID NO:7.

A "FUSCA3 polynucleotide" or "FUS3 polynucleotide" is a nucleic acid sequence comprising (or consisting of) a coding region of about 50 to about 6800 nucleotides, sometimes from about 100 to about 3000 nucleotides and sometimes from about 300 to about 1300 nucleotides, which hybridizes to SEQ ID NO:8, SEQ ID NO:10, SEQ ID NO:11, or SEQ ID NO:13 under stringent conditions (as defined below), or which encodes a FUS3 polypeptide or fragment of at least 15 amino acids thereof. FUS3 polynucleotides can also be identified by their ability to hybridize under low stringency conditions (e.g., Tm ~40° C.) to nucleic acid probes having the sequence of SEQ ID NO:8, SEQ ID NO:10, SEQ ID NO:11 or SEQ ID NO:13. SEQ ID NO:8, SEQ ID NO:10, SEQ ID NO:11 and SEQ ID NO:13 are examples of a FUS3 polynucleotide.

A "FUSCA3 polypeptide" or "FUS3 polypeptide" or "FUS3 protein" is a B3 domain protein. A FUS3 polypeptide has a sequence of about 50 to about 400, sometimes 100 to 300, and preferably 255 amino acid residues encoded by a FUS3 polynucleotide. FUS3 polypeptides are plant transcription factors characterized by the presence of a B3 domain. For instance amino acid residues 78 to 192 represent the B3 domain of the polypeptide shown in SEQ ID NO:9. The B3 domain of FUS3 is a DNA binding domain and is shown in SEQ ID NO:15.

"Increased or enhanced expression or activity of a B3 domain protein," e.g., LEC2 or FUS3 proteins, or "increased or enhanced expression or activity of a nucleic acid encoding a B3 domain protein," e.g., LEC2 or FUS3 genes, refers to an augmented change in activity of the B3 domain protein. Examples of such increased activity or expression include the following: Activity of the B3 domain protein or expression of the gene encoding the B3 domain protein is increased above the level of that in wild-type, non-transgenic control plants (e.g., the quantity of LEC2 or FUS3 activity or expression of the LEC2 or FUS3 gene is increased). Activity of the B3 domain protein or expression of the gene encoding the B3 domain protein is in an organ, tissue or cell where it is not normally detected in wild-type, non-transgenic control plants (i.e. spatial distribution of the B3 domain protein or expression of the gene encoding the B3 domain protein is altered). Activity of the B3 domain protein or expression of the gene encoding the B3 domain protein is increased when activity of the B3 domain protein or expression of the gene encoding the B3 domain protein is present in an organ, tissue or cell for a longer period than in a wild-type, non-transgenic controls (i.e. duration of activity of the B3 domain protein or expression of the gene encoding the B3 domain protein is increased).

"Decreased expression or activity of a B3 domain protein," e.g., LEC2 or FUS3 proteins, or "decreased expression or activity of a nucleic acid encoding a B3 domain protein," e.g., LEC2 or FUS3 genes, refers to a decrease in activity of the B3 domain protein. Examples of such decreased activity or expression include the following: Activity of the B3 domain protein or expression of the gene encoding the B3 domain protein is decreased below the level of that in wild-type, non-transgenic control plants (e.g., the quantity of LEC2 or FUS3 activity or expression of the LEC2 or FUS3 gene is decreased).

The term "reproductive structures" or "reproductive tissues" as used herein includes fruit, ovules, seeds, pollen, flowers, or flower parts such as pistils, stamens, sepals, petals, carpels, or any embryonic tissue.

The term "vegetative structures" or "vegetative tissues" as used herein includes leaves, stems, tubers, roots, vascular tissue, or root and shoot meristem.

An "expression cassette" refers to a nucleic acid construct, which when introduced into a host cell, results in transcription and/or translation of a RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular gene, such as LEC2. In addition, the term specifically includes sequences (e.g., full length sequences) substantially identical (determined as described below) with a gene sequence encoding a B3 domain protein, e.g., LEC2 or FUS3, and that encode proteins that retain the function of a B3 domain protein, e.g., LEC2 or FUS3 polypeptide.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99%. compared to a reference sequence using the programs described herein; preferably BLAST using standard parameters, as described below. Accordingly, sequences encoding a B3 domain protein used in the methods of the present invention include nucleic acid sequences that have substantial identity to SEQ ID NO:1, SEQ ID NO:5, SEQ ID NO:8, SEQ ID NO:10, SEQ ID NO:11, or SEQ ID NO:13. For example LEC2 sequences of the invention include nucleic acid sequences that have substantial identity to SEQ ID NO:1, SEQ ID NO:3 and SEQ ID NO:4. LEC2 sequences of the invention also include polypeptide sequences having substantial identity to SEQ ID NO:2. FUS3 sequences of the invention include nucleic acid sequences that have substantial identity to SEQ ID NO:8, SEQ ID NO:10, SEQ ID NO:11 or SEQ ID NO:13. FUS3 sequences of the invention also include polypeptide sequences having substantial identity to SEQ ID NO:9, SEQ ID NO:12 or SEQ ID NO:14. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 90%, 95%, or 99%. Most preferred embodiments include 61%, 62%, 63%, 64%, 65%, 66%, 67%, 68%, 69%, 70%, 71%, 72%, 73%, 74% and 75%. Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

The term "cytokinin related processes" refers to processes within a plant that are modulated by cytokinin. Examples of cytokinins include, but are not limited to, kinetin, zeatin, benzyl adenine. Examples of cytokinin related processes include processes within a cell affected by cytokinin, e.g., cell division, stress tolerance, drought tolerance, disease resistance, resistance to lodging, senescence, apical dominance, and assimilate partitioning. Modulation of cytokinin related processes can result from, e.g., overproduction of cytokinin, underproduction of cytokinin, increased sensitivity to cytokinin in a cell or decreased sensitivity to cytokinin in a cell.

DETAILED DESCRIPTION OF THE INVENTION

A. General Overview.

The present invention provides new methods of modulating cytokinin related processes in a plant using B3 domain proteins and selecting for plants with phenotypes associated with altered cytokinin related processes. Cytokinin related processes can be modulated by overproducing cytokinin in a plant, underproducing cytokinin in a plant, increasing sensitivity to cytokinin in a plant, or decreasing sensitivity to cytokinin in a plant. The present invention is based, in part, on the surprising discovery that increased expression of a gene that encodes a B3 domain protein, e.g., a LEC2 or FUS3 gene, in a plant induces cytokinin related processes in the plant. Cytokinin related processes include any process affected by cytokinin levels or activity in a plant. Examples of cytokinin related processes include, disease resistance, stress tolerance, drought tolerance, resistance to lodging, delayed senescence, apical dominance, and assimilate partitioning.

Accordingly, the present invention provides new methods of delaying senescence in a plant by overexpressing a B3 domain protein, e.g., a LEC2 or FUS3 protein, in the plant. The present invention also provides methods for selecting for a plant with delayed senescence patterns or characteristics. Delayed senescence patterns result in plants with altered phenotypes as compared to wild type plants. These altered phenotypes include, but are not limited to, modulated (e.g., enhanced) size of plant parts and an increased number of plant parts. Accordingly, by overexpressing a B3 domain protein in a plant, plants with increased biomass and yield can be identified.

The present invention also provides methods of increasing disease resistance in a plant by overexpressing a B3 domain protein, e.g., a LEC2 or FUS3 protein, in the plant and selecting for a plant with an increased disease resistance phenotype. In some embodiments, a plant with increased disease resistance will be healthier and live longer than a wild type plant when exposed to disease conditions. Increased disease resistance can be measured according to any method known to those of skill in the art. For example, disease symptoms in a test plant can be compared to disease symptoms in a control plant following contact with a pathogen.

The present invention also provides methods of increasing stress tolerance in a plant by overexpressing a B3 domain protein, e.g., a LEC2 or FUS3 protein, in the plant and selecting for a plant with an increased stress tolerance phenotype. Examples of these include, e.g., increased tolerance to drought or high salt conditions. In some embodiments, a plant with increased stress tolerance will be able to adapt better to environmental conditions as compared to a wild type plant. For example, a plant with increased drought tolerance will have leaves that retain their turgor in drought conditions.

The present invention also provides methods of increasing resistance to lodging in a plant by overexpressing a B3 domain protein, e.g., a LEC2 or FUS3 protein, in the plant and selecting for a plant with an increased lodging resistant phenotype. In some embodiments, a plant with increased resistance to lodging will have thicker stems as compared to a wild type plant.

B. Isolation of Nucleic Acids Used in the Methods of the Present Invention.

The isolation of sequences from the genes used in the methods of the present invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library that contains the gene transcripts is prepared from the mRNA.

The cDNA or genomic library can then be screened using a probe based upon the sequence of a cloned embryo-specific gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes encoding a B3 domain protein from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). For example, appropriate primers for amplification of the genomic region of LEC2 include the following three primer pairs: D2F-5'TTTCAGAATACGCAAAAACGAC3' (SEQ ID NO:19)and D2R-5'AACTATCCTCCCGAGTGACC3' (SEQ ID NO:20); Ef-5'AGATGGCAAGGATCAACAGG3' (SEQ ID NO:21)and BlastR-5'CTTGCTTTCGTCCTCG-TATATTG3' (SEQ ID NO:22); and F2F-5'TTTGTGAAG-CAAAATGGAGC3' (SEQ ID NO:23)and Stop-5'CGGAT-GAACCCACGTACG3' (SEQ ID NO:24). Appropriate primers for amplification of the LEC2 cDNA include the following pair: 5'AAATGGATAACTTCTTACCCTTTCC3' (SEQ ID NO:25)and 5'CGGATGAACCCACGTACG3' (SEQ ID NO:26). The amplification conditions are typically as follows. Reaction components: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per ml Taq polymerase. Program: 96 C for 3 min., 30 cycles of 96 C for 45 sec., 50 C for 60 sec., 72 for 60 sec, followed by 72 C for 5 min.

Polynucleotides may also be synthesized by well-known techniques as described in the technical literature. See, e.g., Carruthers et al., Cold Spring Harbor Symp. *Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of nucleic acid sequences encoding B3 domain proteins used in the methods of the present invention includes genes and gene products identified and characterized by analysis using the nucleic acid sequences, including SEQ ID NO:1, SEQ ID NO:5, SEQ ID NO:8, SEQ ID NO:10, SEQ ID NO:11 and SEQ ID NO:13 and protein sequences, including SEQ ID NO:2, SEQ ID NO:9, SEQ ID NO:12 and SEQ ID NO:14. Sequences encoding B3 domain proteins used in the present invention include nucleic acid sequences having substantial identity to SEQ ID NO:1, SEQ ID NO:5, SEQ ID NO:8, SEQ ID NO:10, SEQ ID NO:11, and SEQ ID NO:13. Sequences encoding B3 domain proteins used in the present invention include polypeptide sequences having substantial identity to SEQ ID NO:2, SEQ ID NO:9, SEQ ID NO:12 and SEQ ID NO:14. B3 domains used in the present invention include sequences having substantial identity to SEQ ID NO:7, SEQ ID NO:15, SEQ ID NO:16, SEQ ID NO:17 and SEQ ID NO:18.

The nucleic acids of the present invention encode B3 domain proteins. B3 domain proteins fall into different classes or families depending upon the relationship between their encoded B3 domains. Accordingly, in some embodiments of the present invention, the nucleic acids used in the methods of the present invention will encode a B3 domain identical or substantially identical to a specific class or family of B3 domain proteins, e.g., B3 domain-containing transcription factors. In some embodiments, the B3 domain-containing transcription factors bind to a RY motif, e.g., the wild type RY motif CATGCATG, see, e.g., Reidt et al., *Plant J.,* 21(5), 401-408 (2000). Those of skill will recognize that B3 domain proteins can be screened for the ability to bind RY motifs using standard assays, such as gel-shift or DNA footprinting assays, see, e.g., Maniatis et al., Molecular Cloning, Cold Spring Harbor (1982).

SEQ ID NOS:11-13 illustrate conserved B3 domain motifs. Examples 5 and 6 provide alignments of B3 proteins and illustrate additional possible amino acids in non-conserved positions. Thus, in some embodiments, B3 domains comprise the amino acids that are either conserved or similar as defined in BLAST algorithms between any of LEC2, FUS3 VP1, or as illustrated as gray boxes in Examples 5-6.

Alternatively, in some embodiments, the B3 domain-containing transcription factors regulate embryogenesis in plants. The B3 domain proteins may be preferentially expressed in a plant cell at certain developmental stages, e.g., embryogenesis. In some embodiments of the present invention, the nucleic acids used in the methods of the present invention will encode a B3 domain characteristic of the LEC2/FUS3-like proteins. For example, in some embodiments, the B3 domain protein will comprise a B3 domain identical or substantially identical to the B3 domain found in LEC2 or FUS3. In other embodiments, the B3 domain protein will be identical or substantially identical to the LEC2 or FUS3 polypeptides as shown in SEQ ID NOS: 2 and 9. Alternatively, in some embodiments, a B3 domain protein used in the present invention will have a B3 domain characteristic of the VP1/ABI3-like proteins but will not have other regions, e.g., masking motifs, of the protein that prevent binding with DNA. Examples of these masking motifs include amino acid residues 1 to 491 and 632 to 659 present in the VP1 protein, see, Suzuki et al., *Plant Cell,* 9:799-807 (1997).

Once a nucleic acid is isolated using the method described above, standard methods can be used to determine if the nucleic acid encodes a B3 domain protein. Nucleic acids that encode B3 domain proteins can be used to create transgenic plants having delayed senescence. In some embodiments of the present invention, the B3 domain will be identical or substantially identical to SEQ ID NO: 7 or SEQ ID NO:15. In other embodiments, the B3 domain will be identical or substantially identical to the conserved regions of SEQ ID NO: 16, SEQ ID NO:17 or SEQ ID NO:18. A transgenic plant having enhanced or increased expression of a B3 domain protein identical or substantially identical to SEQ ID NO:2, SEQ ID NO:9, SEQ ID NO:12 or SEQ ID NO:14 will display a phenotype associated with an altered cyotkinin process within the plant, e.g., delayed senescence.

Alternatively, the B3 domain may be identical or substantially identical to the LEC2 B3 domain as described in SEQ ID NO:7 or the FUS3 B3 domain as described in SEQ ID NO:15. The skilled practitioner will understand that a nucleic acid encoding a B3 domain identical or substantially identical to SEQ ID NO:7, SEQ ID NO:15, SEQ ID NO:16, SEQ ID NO:17 or SEQ ID NO:18 can be used in the methods of the present invention to create a plant with a phenotype associated with an altered cytokinin process with in the plant, e.g., a phenotype associated with delayed senescence.

In other embodiments, the nucleic acid will encode a LEC2 polypeptide identical or substantially identical to SEQ ID NO:2. Alternatively, in even other embodiments, the nucleic acid will encode a FUS3 polypeptide identical or substantially identical to SEQ ID NO:9, SEQ ID NO:12, or SEQ ID NO:14.

Using standard methods, the skilled practitioner can compare the sequence of a putative nucleic acid sequence thought to encode a B3 domain protein to a nucleic acid sequence encoding a B3 domain protein to determine if the putative nucleic acid encodes a B3 domain. Nucleic acids that encode a B3 domain protein, e.g., nucleic acids comprising sequences identical or substantially identical to the B3 domains as shown in SEQ ID NOs: 7, 15, 16, 17, and 18 can be used in the methods of the present invention.

C. Enhancing Expression of B3 Domain Proteins.

The present invention provides methods of modulating cytokinin related processes in a plant. In one embodiment of the invention, cytokinin related processes are modulated by increasing or enhancing expression of gene encoding a B3 domain protein in a plant, e.g., LEC2 or FUS3 genes. For example, in some embodiments, the present invention provides methods of delaying senescence in a plant by increasing or enhancing expression of a gene encoding a B3 domain protein in a plant, e.g., LEC2 or FUS3 genes. A plant with delayed senescence possesses phenotypic characteristics that are recognizable to the skilled practitioner, e.g., abnormal developmental patterns such as larger plant parts and/or an enhanced number of plants parts. The affected plant part can be a reproductive plant part or vegetative plant part. For example, the plant part may include, but is not limited to, fruit, ovules, seeds, pollen, embryonic tissue, flowers, flower parts such as pistils, stamens, sepals, petals, carpels, leaves, stems, tubers, roots, vascular tissue, provascular tissue or root or stem meristem.

In other embodiments, the present invention provides methods of increasing disease resistance in a plant and selecting for a plant with an increased disease resistance phenotype. A plant with increased disease resistance will have phenotypic characteristics that are recognizable to the skilled practitioner, e.g., reduced symptoms following exposure to a pathogen.

The nucleic acids described in the present invention may also be used to increase stress tolerance in a plant. Accordingly, the present invention provides methods of increasing stress tolerance in a plant and selecting a plant with an increased stress tolerance phenotype. A plant with increased stress tolerance will have phenotypic characteristics that are recognizable to the skilled practitioner, e.g., increased drought tolerance.

Methods of increasing resistance to lodging in a plant or decreasing apical dominance are also embodied in the present invention.

Using specified promoters, the skilled practitioner can direct the expression of a B3 domain protein, e.g., LEC2, and create plants with desirable phenotypic characteristics. For example, in some embodiments of the present invention, a tissue specific promoter, such as a seed specific promoter, can be used to create a transgenic plant with altered seed characteristics as compared to a wild type plant. A plant with altered seed characteristics, for example, may have greater seed yield or larger seeds as compared to a wild type plant. In other embodiments, the desirable characteristic may be a plant with an increased number of flowers as compared to a wild type plant. Accordingly, the skilled practitioner may use a floral specific promoter to create a transgenic plant with the desired characteristic. Similarly, the skilled practitioner can choose from a variety of known promoters, whether constitutive, inducible, tissue-specific, and the like to drive expression of the gene encoding the B3 domain protein, e.g., LEC2 or FUS3 gene, thereby delaying senescence in a plant. Other desirable phenotypic characteristics may include leaves that stay green longer or a plant with an increased yield of fruit or an increased number of stems.

Any phenotypic characteristic caused by alteration of cytokinin related processes in a plant, e.g., delayed senescence, can be selected for in the present invention. For example, after introducing a polynucleotide encoding a B3 domain protein, operably linked to a desirable promoter, e.g., constitutive, tissue specific, or inducible, in a plant, and regenerating the plant by standard procedures, a skilled practitioner can use standard methods to determine if the transgenic plant is a transgenic plant of the present invention, e.g., by comparing the transgenic plant to a wild type plant and looking for phenotypes associated with an alteration of cytokinin related processes, e.g., delayed senescence. In some embodiments of the present invention, the plant will be characterized by delayed ovule senescence. Delayed ovule senescence may be evident by an ovule increased in size as compared to a wild type ovule or ovule development in the absence of fertilization.

Enhancing or increasing expression of a gene encoding a B3 domain protein in a plant may modulate cytokinin related processes by a variety of pathways. The particular pathway used to modulate cytokinin related processes is not critical to the present invention. For example, overexpression of a B3 domain protein in a plant may affect cytokinin related processes by increasing cytokinin levels in a plant, increasing sensitivity to cytokinin in a plant, decreasing cytokinin levels in a plant or decreasing sensitivity to cytokinin in a plant.

Any number of means well known in the art can be used to increase activity of a B3 domain protein, e.g., a LEC2 polypeptide, in a plant. For example, the sequences, as described herein, can be used to prepare expression cassettes that enhance or increase endogenous gene expression. Where overexpression of a gene is desired, the desired gene from a different species may be used to decrease potential sense suppression effects. Enhanced expression of polynucleotides encoding B3 domains, is useful, for example, to increase the number of seeds produced by a plant. Such techniques may be particularly useful for increasing the yield of important plant crops.

Any organ can be targeted for overexpression of a B3 domain protein, e.g., LEC2 or FUS3, such as shoot vegetative organs/structures (e.g., leaves, stems, and tubers), roots, flowers, and floral or reproductive organs/structures (e.g., bracts, sepals, petals, stamens, carpels, anthers and ovules), seed (including embryo, endosperm, and seed coat) and fruit. Vascular or provascular tissues may be targeted. Alternatively, one or several genes described in the present invention may be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

D. Inhibiting Expression of B3 Domain Proteins.

In some embodiments of the present invention, cytokinin related processes are modulated by inhibiting gene expression in a plant. For example, expression cassettes of the invention can be used to suppress endogenous expression of genes encoding a B3 domain protein, e.g., FUS3 or LEC2. Reducing the activity of cytokinin related processes may increase apical dominance, leading to less branching, or may promote root growth.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the protein of interest, see, e.g., Sheehy et al., *Proc. Natl. Acad. Sci. USA*, 85:8805-8809 (1988), and Hiatt et al., U.S. Pat. No. 4,801,340.

The antisense nucleic acid sequence transformed into plants will be substantially identical to at least a portion of the endogenous embryo-specific gene or genes to be repressed. The sequence, however, does not have to be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Transposon insertions or tDNA insertions can be used to inhibit expression of genes encoding B3 domain proteins. Standard methods are known in the art. Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585-591 (1988).

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Another means of inhibiting gene function in a plant is by creation of dominant negative mutations. In this approach, non-functional, mutant B3 domain polypeptides, which retain the ability to interact with wild-type subunits are introduced into a plant.

E. Preparation of Recombinant Vectors.

To use isolated sequences in the above techniques, recombinant DNA vectors suitable for transformation of plant cells are prepared. Techniques for transforming a wide variety of higher plant species are well known and described in the technical and scientific literature, e.g., Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters), organ (organ-specific promoters) or may be otherwise under more precise environmental control (inducible promoters). Examples of tissue-specific promoters under developmental control include promoters that initiate transcription only in certain tissues, such as fruit, seeds, flowers, pistils, or anthers. Suitable promoters include those from genes encoding storage proteins or the lipid body membrane protein, oleosin. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Nucleic acid sequences of the invention, e.g., nucleic acid sequences that encode B3 domain proteins, are expressed recombinantly in plant cells to enhance and increase levels of endogenous plant transcription factors. For example, LEC2 or FUS3 nucleic acid sequences of the invention are expressed recombinantly in plant cells to enhance and increase levels of endogenous LEC2 or FUS3 polypeptides. A variety of different expression constructs, such as expression cassettes and vectors suitable for transformation of plant cells can be prepared. Techniques for transforming a wide variety of higher plant species are well known and described in the technical and scientific literature, e.g., Weising et al. *Ann. Rev. Genet.* 22:421-477 (1988). A DNA sequence coding for a polypeptide described in the present invention, e.g., a cDNA sequence encoding a full length LEC2 protein, can be combined with cis-acting (promoter and enhancer) transcriptional regulatory sequences to direct the timing, tissue type and levels of transcription in the intended tissues of the transformed plant. Translational control elements can also be used.

The invention provides a nucleic acid encoding a B3 domain protein operably linked to a promoter which, in some embodiments, is capable of driving the transcription of the coding sequence in plants. The promoter can be, e.g., derived from plant or viral sources. The promoter can be, e.g., constitutively active, inducible, or tissue specific. In construction of recombinant expression cassettes, vectors, transgenics, of the invention, different promoters can be chosen and employed to differentially direct gene expression, e.g., in some or all tissues of a plant or animal. Typically, as discussed above, desired promoters are identified by analyzing the 5' sequences of a genomic clone corresponding to the embryo-specific genes described here.

Constitutive Promoters

A promoter fragrnent can be employed which will direct expression of a nucleic acid encoding a B3 domain protein, e.g., LEC2 or FUS3, in all transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless (1997) *Arch. Virol.* 142:183-191); the 1'- or 2'-promoter derived from T-DNA of *Agrobacterium tumefaciens* (see, e.g., Mengiste (1997) supra; O'Grady (1995) *Plant Mol. Biol.* 29:99-108); the promoter of the tobacco mosaic virus; the promoter of Figwort mosaic virus (see, e.g., Maiti (1997) *Transgenic Res.* 6:143-156); actin promoters, such as the *Arabidopsis* actin gene promoter (see, e.g., Huang (1997) *Plant Mol. Biol.* 33:125-139); alcohol dehydrogenase (Adh) gene promoters (see, e.g., Millar (1996) *Plant Mol. Biol.* 31:897-904); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251: 196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol.* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf (1995) "Comparison of different constitutive and inducible promoters for the overexpression of transgenes in *Arabidopsis thaliana,*" *Plant Mol. Biol.* 29:637-646.

Inducible Promoters

Alternatively, a plant promoter may direct expression of the nucleic acids described in the present invention, e.g., nucleic acids encoding a B3 domain protein, under the influence of changing environmental conditions or developmental conditions. Examples of environmental conditions that may effect transcription by inducible promoters include anaerobic conditions, elevated temperature, drought, or the presence of light. Example of developmental conditions that may effect transcription by inducible promoters include senescence and embryogenesis. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897-909). Examples of developmental conditions include cell aging, and embryogenesis. For example, the invention incorporates the senescence inducible promoter of *Arabidopsis*, SAG 12, (Gan and Amasino, *Science,* 270:1986-1988 (1995)) and the embryogenesis related promoters of LEC1 (Lotan et al., *Cell,* 93:1195-205 (1998)), LEC2 (Stone et al., *Proc. Natl. Acad. of Sci.,* 98:11806-11811 (2001)), FUS3 (Luerssen, *Plant J.* 15:755-764 (1998)), AtSERK1 (Hecht et al. *Plant Physiol* 127:803-816 (2001)), AGL15 (Heck et al. *Plant Cell* 7:1271-1282 (1995)), and BBM (BABYBOOM).

Alternatively, plant promoters which are inducible upon exposure to plant hormones, such as auxins or cytokinins, are used to express the nucleic acids of the invention. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902). The invention can also use the cytokinin inducible promoters of ARR5 (Brandstatter and Kieber, *Plant Cell*, 10:1009-1019 (1998)), ARR6 (Brandstatter and Kieber, *Plant Cell*, 10:1009-1019 (1998)), ARR2 (Hwang and Sheen, *Nature*, 413:383-389 (2001)), the ethylene responsive promoter of ERF1 (Solano et al., *Genes Dev.* 12:3703-3714 (1998)), and the β-estradiol inducible promoter of XVE (Zuo et al., *Plant J*, 24:265-273 (2000)).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) *Plant Cell Physiol.* 38:568-577) as well as the promoter of the glucocorticoid receptor protein fusion inducible by dexamethasone application (Aoyama, *Plant J.*, 11:605-612 (1997)); application of different herbicide safeners induces distinct gene expression patterns, including expression in the root, hydathodes, and the shoot apical meristem. The coding sequence of the described nucleic acids can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324).

Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol.* 22:10131-1038); vivparous-1 from *Arabidopsis* (Genbank No. U93215); atmyc1 from *Arabidopsis* (Urao (1996) *Plant Mol. Biol.* 32:571-57; Conceicao (1994) *Plant* 5:493-505); napA and BnCysP1 from *Brassica napus* (GenBank No. J02798, Josefsson (1987) JBL 26:12196-1301, Wan et al., *Plant J* 30:1-10 (2002)); and the napin gene family from *Brassica napus* (Sjodahl (1995) *Planta* 197:264-271). Fruit specific promoters include the promoter from the CYP78A9 gene (Ito and Meyerowitz, *Plant Cell*, 12:1541-1550 (2000)).

The ovule-specific BEL1 gene described in Reiser (1995) *Cell* 83:735-742, GenBank No. U39944, can also be used. See also Ray (1994) *Proc. Natl. Acad. Sci. USA* 91:5761-5765. The egg and central cell specific FIE1 promoter is also a useful reproductive tissue-specific promoter.

Sepal and petal specific promoters are also used to express nucleic acids encoding a B3 domain protein in a reproductive tissue-specific manner. For example, the *Arabidopsis* floral homeotic gene APETALA1 (AP1) encodes a putative transcription factor that is expressed in young flower primordia, and later becomes localized to sepals and petals (see, e.g., Gustafson-Brown (1994) *Cell* 76:131-143; Mandel (1992) *Nature* 360:273-277). A related promoter, for AP2, a floral homeotic gene that is necessary for the normal development of sepals and petals in floral whorls, is also useful (see, e.g., Drews (1991) *Cell* 65:991-1002; Bowman (1991) *Plant Cell* 3:749-758). Another useful promoter is that controlling the expression of the unusual floral organs (ufo) gene of *Arabidopsis*, whose expression is restricted to the junction between sepal and petal primordia (Bossinger (1996) *Development* 122:1093-1102).

A maize pollen-specific promoter has been identified in maize (Guerrero (1990) *Mol. Gen. Genet.* 224:161-168). Other genes specifically expressed in pollen are described, e.g., by Wakeley (1998) *Plant Mol. Biol.* 37:187-192; Ficker (1998) *Mol. Gen. Genet.* 257:132-142; Kulikauskas (1997) *Plant Mol. Biol.* 34:809-814; Treacy (1997) *Plant Mol. Biol.* 34:603-611.

Promoters specific for pistil and silique valves, inflorescence meristems, cauline leaves, and the vasculature of stem and floral pedicels include promoters from the FUL gene Mandel and Yanofsky, *Plant Cell*, 7:1763-1771 (1995). Promoters specific for developing carpels, placenta, septum, and ovules are also used to express LEC2 nucleic acids in a tissue-specific manner. They include promoters from the SHP1 and SHP2 genes (Flanagan et al. *Plant J* 10:343-353 (1996), Savidge et al., *Plant Cell* 721-733). Promoters specific for the anther tapetum may be derived from the TA29 gene (Goldbeg et al., *Philos Trans. R. Soc. Lond. B. Biol. Sci.* 350:5-17).

Other suitable promoters include those from genes encoding embryonic storage proteins. For example, the gene encoding the 2S storage protein from *Brassica napus*, Dasgupta (1993) *Gene* 133:301-302; the 2s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212, Lee (1994) *Plant Mol. Biol.* 26:1981-1987; and, the gene encoding low molecular weight sulphur rich protein from soybean, Choi (1995) *Mol Gen, Genet.* 246:266-268, can be used. The tissue specific E8 promoter from tomato is particularly useful for directing gene expression so that a desired gene product is located in fruits. Suitable promoters may also include those from genes expressed in vascular tissue, such as the ATHB-8, AtPIN1, AtP5K1 or TED3 genes (Baima et al., *Plant Physiol.* 126:643-655 (2001), Galaweiler et al., *Science*, 282:2226-2230 (1998), Elge et al., *Plant J.*, 26:561-571 (2001), Igarashi et al., *Plant Mol. Biol.*, 36:917-927 (1998)).

A tomato promoter active during fruit ripening, senescence and abscission of leaves and, to a lesser extent, of flowers can be used (Blume (1997) *Plant J.* 12:731-746). Other exemplary promoters include the pistil specific promoter in the potato (*Solanum tuberosum* L.) SK2 gene, encoding a pistil-specific basic endochitinase (Ficker (1997) *Plant Mol. Biol.* 35:425-431); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the nucleic acids used in the methods of the invention. For example, promoters controlling patatin, the major storage protein of the potato tuber, can be used, e.g., Kim (1994) *Plant Mol. Biol.* 26:603-615; Martin (1997) *Plant J.* 11:53-62. The ORF13 promoter from *Agrobacterium rhizogenes* which exhibits high activity in roots can also be used (Hansen (1997) *Mol. Gen. Genet.* 254:337-343). Other useful vegetative tissue-specific promoters include: the tarin promoter of the gene encoding a globulin from a major taro (Colocasia esculenta L. Schott) corm protein family, tarin (Bezerra (1995) *Plant Mol. Biol.* 28:137-144); the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91-95). A ribulose bisphosphate carboxylase promoters expressed almost exclusively in mesophyll cells in leaf blades and leaf sheaths at high levels, described by Matsuoka (1994) *Plant J.* 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (Atmyb5) described by Li (1996) *FEBS Lett.* 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16-cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423-433; and, Long (1996) *Nature* 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517-527). Also useful are knl-related genes from maize and other species which show meristem-specific expression, see, e.g., Granger (1996) *Plant Mol. Biol.* 31:373-378; Kerstetter (1994) *Plant Cell* 6:1877-1887; Hake (1995) *Philos. Trans. R. Soc. Lond. B. Biol. Sci.* 350:45-51. For example, the *Arabidopsis thaliana* KNAT1 or KNAT2 promoters. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln (1994) *Plant Cell* 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a nucleic acid described in the present invention is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679-1683) the rice tungro bacilliform virus (RTBV), which replicates only in phloem cells in infected rice plants, with its promoter which drives strong phloem-specific reporter gene expression; the cassaya vein mosaic virus (CVMV) promoter, with highest activity in vascular elements, in leaf mesophyll cells, and in root tips (Verdaguer (1996) *Plant Mol. Biol.* 31:1129-1139).

F. Production of Transgenic Plants.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al. *Proc. Natl. Acad. Sci. USA* 82:5824 (1985). Biolistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. The LEC2 genes of the invention are particularly useful in the production of transgenic plants in the genus *Brassica*. Examples include broccoli, cauliflower, brussel sprouts, canola, and the like.

G. Detection of the Transgenic Plants of the Present Invention.

Using known procedures, one of skill can screen for plants of the invention by detecting increased or decreased levels of B3 domain proteins in a plant and detecting the desired phenotype. Means for detecting and quantifying mRNA or proteins are well known in the art, e.g., Northern Blots, Western Blots or activity assays. For example, after introduction of the expression cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be examined for any of the phenotypic characteristics associated with altered cytokinin related processes, e.g., characteristics associated with delayed senescence. For example, using the methods of the present invention, overexpression of the nucleic acids or proteins described in the present invention, e.g., B3 domain proteins such as LEC2 or FUS3, may delay senescence in cells of a vegetative or reproductive plant structure. The skilled practitioner can use standard methods to determine if a plant possesses the characteristics associated with delayed senescence. For example, leaf color can be examined to determine if the photosynthetic life-span of the plant has been effected. Plants with extended photosynthetic life cycles are characterized by leaves that stay green for a longer duration of time as compared to wild type plants. The size of plant vegetative and reproductive structures can be examined to determine if they are larger or smaller than those of a wild type plant. Transgenic plants of the present invention may possess larger fruit, ovules, seeds, pollen, embryonic tissue, flowers, flower parts such as pistils, stamens, sepals, petals, carpels, leaves, stems, tubers, roots, vascular tissue, provascular tissue or root or stem meristems. In other embodiments, transgenic plants of the present invention may have decreased internode elongation, smaller leaves, smaller fruits or a smaller size as compared to a wild type plant.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Overexpression of LEC2

LEC2 cDNA fused with the 35S CaMV promoter was transferred into lec2-1 and lec2-5 mutants and into wild type Ws-0 plants using the *Agrobacterium* floral dipping method. Similar overexpression phenotypes were observed in mutant and wild type backgrounds. Fleshy embryo-like T1 seedlings with unexpanded cotyledons and unextended hypocotyls and radicles were often obtained on hormone-free medium. These, as well as other more wild type looking seedlings, produced calli. Somatic embryos, cotyledon-like organs, leaves and shoots often emerged from calli. Roots were induced less regularly, were sometimes abnormal in thickness, anatomy and color, and were sometimes ectopically induced on leaf and floral organs. Somatic embryos readily germinated and further induced the production of callus, somatic embryos, and vegetative organs, which lead to the formation of large plantlet masses. In contrast to excised wild type leaves that senesced when cultured on hormone-free medium, 35S::LEC2 leaves did not senesce, and instead induced the formation of calli, leaves, shoots, cotyledon-like organs, somatic embryos, and occasionally roots. These phenotypes indicate that LEC2 is capable of establishing embryogenic competence in cells. In addition, ectopic expression of LEC2 creates a proliferative organogenic environment. T1 seedlings containing the 35S::LEC2 transgene with good root growth were transferred to soil and subsequently developed into plants with small stature, small leaves, thicker stems, limited internode elongation, reduced apical dominance, and floral abnormalities including male sterility. These 35S::LEC2 plants remained green and continued to grow long after wild type plants of the same age had died, indicating a delay in leaf and stem senescence.

One of the most striking phenotypes of 35S::LEC2 T1 plants grown on soil is the continued growth of ovules in the absence of fertilization. Wild type ovule embryo sacs and integument cells collapsed by 10 days post-anthesis in the absence of fertilization. Conversely, unfertilized 35S::LEC2 ovules did not senesce, and usually grew larger than wild type seeds. Ovule growth was strictly due to integument cell division and enlargement; the embryo sac did not persist. This is the first observation of unfertilized, non-senescent ovules in *Arabidopsis*.

Pollinated 35S::LEC2 pistils developed into siliques that were shorter and wider than wild type. At 20 days after pollination, 35S::LEC2 siliques remained green and non-dehiscent whereas wild type siliques had yellowed and were beginning to dehisce. Thus, 35S::LEC2 delayed silique senescence. Unpollinated 35S::LEC2 pistils that enclosed the growing ovules elongated and developed into structures with characteristics similar to 35S::LEC2 siliques. In the absence of pollination, wild type pistils elongated only slightly prior to their senescence around 10 days post anthesis. These results indicate that the presence of LEC2 circumvents normal pistil death that occurs in the absence of pollination and delays the senescence of the resulting fruit structures.

35S::LEC2 T1 plants that were pollinated with wild type pollen formed siliques in which the majority of seeds were larger than wild type, and all had fleshy seed coats. Embryos within these seeds were usually varied in shape, but most were larger than wild type in size. Embryo size and shape did not segregate into discrete categories, and did not appear to be associated with the presence of the transgene in the embryo. The fleshy seed coats result from continued cell divisions and the delay in cell death that normally occurs during maturation in wild type seed coats. Reciprocal cross experiments in which wild type plants were pollinated with 35S::LEC2 pollen resulted in 100% wild type looking seeds and embryos. These results indicate that LEC2 affects both seed size and shape through its expression in maternally-derived tissues. The delayed senescence of the 35S::LEC2 silique allows all its seeds, regardless of whether the embryo contains the 35S::LEC2 transgene, to continue to grow longer than wild type and, thus, to achieve a larger size.

Taken together, the increased life span of the 35S::LEC2 whole plants, siliques, ovules, and seeds, and the lack of senescence of ovules in unpollinated pistils and excised leaves indicate that LEC2 is sufficient to delay senescence.

Example 2

Cytokinin Associated Delay in Senescence

An increase in cytokinins either by exogenous application or by increasing endogenous levels is often associated with a delay in senescence. We used a GUS reporter gene under the control of a promoter from the cytokinin inducible gene, ARR5 (Agostino et al. (2000) *Plant Physiol* 124: 1706), to indirectly identify changes in the level of or sensitivity to cytokinins. Both wild type and 35S::LEC2 pistils at anthesis had similar levels of ARR5 regulated GUS activity in septa and funiculi and appeared to be associated with vascular tissues. At 5 days post anthesis, 35S::LEC2 unpollinated pistils maintained this level of ARR5 promoter activity in septa and funiculi similar to wild type pollinated siliques, whereas wild type pistils at the same age displayed lower levels of ARR5 promoter activity in these tissues. In pollinated siliques at late stages of seed development, 35S::LEC2 siliques displayed higher levels of ARR5 promoter activity than did wild type siliques. These results suggest that the prolonged growth of 35S::LEC2 unpollinated ovules and seeds result from delayed senescence of the ovule and seeds, perhaps due to an increase in the expression of cytokinin inducible genes.

Example 3

Overexpression of FUS3

FUS3 cDNA fused with the 35S CaMV promoter was transferred into wild type *Arabidopsis* plants, ecotype Ws-0, using the *Agrobacterium* floral dipping method. Two types of transformed seedlings were obtained on hormone-free medium. Approximately 50% of the transformants looked like wild type seedlings except that they had slightly thicker leaves and reduced number of trichomes. The remaining 50% were in comparison delayed in their germination and were abnormal in various ways. A prominent abnormality was the delay in root growth. Therefore, these seedlings were maintained on hormone-free media. Cotyledon-like structures and fleshy leaves often grew out from the cotyledons, the shoot apical meristem and the petioles of these seedlings. Some calli were sometimes obtained that later differentiated into stems, leaves and inflorescences and, on rarer occasions, somatic embryos. Somatic embryos were most often formed at the margin of leaves, as well as stems and floral organs in contact with the media. Somatic embryos germinated and gave rise to vegetative organs, calli, cotyledon-like structures, and, more rarely, somatic embryos, thus leading to the formation of plantlet masses. In contrast to excised wild type organs that senesced when cultured on hormone-free medium, 35S::FUS3 organs did not senesce, and instead induced the formation of leaves, shoots, calli, cotyledon-like organs and somatic embryos. These phenotypes indicate that FUS3 is sufficient to establishing embryogenic competence in cells, conferring embryonic characteristics to seedlings and inducing somatic embryo formation. FUS3 also delays senescence of plant organs. In addition, ectopic expression of FUS3 creates a proliferative, organogenic environment.

T1 seedlings containing the 35S::FUS3 transgene with good root growth were transferred to soil. Most of the seedlings developed into plants with reduced stature, limited internode elongation, lack of apical dominance, and floral abnormalities including male sterility. Most of the transformants remained green and continued to grow long after wild type plants of the same age had died, indicating a delay in leaf and stem senescence.

The transformants with the most severe lack of apical dominance and delay in senescence showed an interesting flower phenotype: stigmatic papilla were absent or barely started to initiate several days postanthesis. One interpretation of this phenotype could be a delay in the maturation of the gynoecium. No seed were ever obtained from these flowers because the male and female reproductive parts developed asynchronously. However, by contrast to wild type, ovules contained in these 35S::FUS3 carpels did not senesce and degenerate. Rather, the 35S::FUS3 ovules increased in size, indicating a delay in ovule senescence and the induction of ovule cell growth and proliferation. Unpollinated 35S::FUS3 pistils that enclosed the enlarged ovules elongated and had thicker, fleshier walls than wild type unpollinated pistils or developing silique walls. Eventually, the fruit structures senesced and the valves yellowed but the replum and septums usually remained green and fleshy for a longer period of time. These results indicate that the presence of FUS3 circumvents normal pistil death that occurs in the absence of pollination and delays the senescence of the resulting fruit structures.

Flowers sometimes reverted to a more wild type development, which allowed fertilization and seed development. In most of the fertile T1 plants, seed development occurred normally, although siliques elongation was often reduced. The fertile 35S::FUS3 plants produced seeds that were undistinguishable from wild type seeds in morphology and viability.

Taken together, the increased life span of the 35S::FUS3 whole plants and the lack of senescence of ovules in unpollinated pistils and excised organs indicate that ectopic FUS3 expression delays senescence.

Example 4

Comparison of LEC2 and FUS3 B3 Domains

ISEQ GAP run using LEC2 and FUS3 B3 domain sequences. The B3 domains of LEC2 and FUS3 share 50% identity and 61.7% similarity.

| B3 domain nt cDNA | B3 domain nt cDNA | % identity | |
|---|---|---|---|
| FUS3 Col | FUS3 Ws-0 | 99.71% | |
| FUS3 Col | FUS3 Ler | 99.71% | |
| FUS3 Ws-0 | FUS3 Ler | 100% | |
| LEC2 Ws-0 | FUS3 Ws-0 | 56.232% | |
| LEC2 Ws-0 | FUS3 Col | 56.232% | |
| B3 domain aa | B3 domain aa | % identity | % similarity |
| LEC2 Ws-0 | FUS3 Col | 50.435% | 61.739% |
| FUS3 Col | FUS3 Ws-0 | 100% | 100% |
| FUS3 Col | FUS3 Ler | 100% | 100% |

FUS3 nucleotide sequences differ in the three *Arabidopsis* ecotypes. However, the polymorphisms do not cause amino acid differences within the B3 domain.

Example 5

Consensus Sequence for LEC2/FUS3/ABI3/VP1 B3 Domains

The following amino acid alignment of residues from the B3 domains of LEC2 (SEQ ID NO:7), FUS3 (SEQ ID NO:15), ABI3 (SEQ ID NO:27), and VP1 (SEQ ID NO:28) was created. Residues in black boxes are identical in at least two of the four proteins, and those in the shaded boxes share similarity with the conserved residues. Numbers in the right column indicate residue numbers in the predicted polypeptides.

```
LEC2   QQSTFDNKKLRVLCEKELKKSDVGSLGRIV   187
FUS3   PSRKIDPEKLRFLEQKELKNSDVSSLRRKK   107
ABI3   QGWKPE..KNLRFLLQKVLKKSDVGNLGRIV   588
VP1    QCAKAD..KNLRFLLQKVLKKSDVGSLGRIV   533

LEC2   LPKKAAEANLPKLSDKKGIVKQMRDKFSMQ   217
FUS3   LPKKAAEAHLPALECKKGIPIRMEDKDGFH   137
ABI3   LPKKEABTHLPELEAKKGISKAMEDIGTSR   618
VP1    LPKKEABVHLPELKTKKGISIPMEDIGTSR   563

LEC2   SWSFKYRKEWSNNKSRMYKLENTGKFVKQNG   247
FUS3   VWTFKYRKWPNNNSRMYKLENTGKFVNAHG   167
ABI3   VWNMKYRFWPNNKSRMYKLENTGKFVKKNG   648
VP1    VWNMKYRFWPNNKSRMYKLENTGKFVKKNE   593

LEC2   AEIGDFKTIYEDESKNLYFAMNGNS        272
FUS3   LQLGDFIKKYQDKYSNNYKIQARKA        192
ABI3   LQEGDFIVIYSDVKCGKYLIRGVKV        673
VP1    LQEGDFIVIYSDVKSGKYLIRGVKV        618
```

Example 6

Consensus Sequence for LEC2 B3 Domain Family

The following amino acid alignment of residues from the B3 domains of AT2G30470 (SEQ ID NO:29) (GenBank Accession No. AAB63089), AT4G32010 (SEQ ID NO:30) (GenBank Accession No. CAA16588), AT4G21550 (GenBank Accession No. CAA18719), FUS3 (SEQ ID NO:32), ABI3 (SEQ ID NO:33) and LEC2 (SEQ ID NO:7) were created. Residues in darkly shaded boxes are identical in all six proteins. Residues in black boxes are identical in at least three of the six proteins, and those in the lightly shaded boxes share similarity with the conserved residues. Numbers in the right column indicate residue numbers in the predicted polypeptides. Consensus sequence=SEQ ID NO:34.

```
AT2G30470   .....NLNLNKVPLFEKTLSASKACKKGKLV
AT4G32010   TVYFPSSNSKKIPLFEKVLSASKACKKGKLV
AT4G21550   IDTTLKYNFK.......LSAKKTCK...KLV
FUS3        PARKIK.PSKKRFLEQKELKNSKVSSLRKK    107
ABI3        QGWKPE..KNLRFLLQKVLKQSKVGNLGKK    588
LEC2        QQSTFK.NKKRVLCEKELKNSKVGSLGKV    187
CONSENSUS   xxxxxxxxxxxxxxxxxxLxxxDxxxxxRxx AT2G30470   KKACKAKFKPKSQSEKIPIKKQKNRG.K
AT4G32010   KKACKAKFKPKSLPEKKPIKKQKKG.K
AT4G21550   KKYAKASKQLSHTKKKPLTKQKPMG.K
FUS3        KAAKAHKDALECKEKKIETRVEDKDGFH     137
ABI3        KKEKKTHKPELEAKKKISLAMEKKGTSK     618
LEC2        KKRDKAKNLKKLSDKKEKIVVQMRKKFSMQ   217
CONSENSUS   LPKxxAExxxPxxxxxxGxxxxxxDxxxxx AT2G30470   EKKFQKPRKWPNNNSRMYVLEGVTPCKQKKM
AT4G32010   EKVFQKRFWPNNNSRMYVLEGVTPCKQKKQ
AT4G21550   EKRFQKRFWPSSKGRKYVLEGVTPKKQKKQ
FUS3        VKKFKKRKWPNNNSRMYVLENTGDKKAHG   167
ABI3        VKNMKRFWPNNKSRMYKLENTGDKKKNG   648
LEC2        SKKFKKYKFWSNNKSRMYVLENTGEKKQNG   247
CONSENSUS   xWxxxxxxxWxxxxxxRxYxLExxxxxxxxx AT2G30470   LQAGDTVTKKSRKKPGGKLKKMGSRK
AT3G32010   LQAGDTVTKKSRTKPEGKLKMGYRK
AT4G21550   LQAGDTVIKKSRBKPERKLKKGFRK
FUS3        LQLGDFKMKKQDKYSNNY.KKQRKK        192
ABI3        LQEGDFKVKKSDKKCGKY.KKRKVK        673
LEC2        AEIGDFKIKKEDESKNLYFAMNKNS        272
CONSENSUS   xxxGDxxxxxxxxxxxxxxxxxxxx
```

What is claimed is:

1. A method of delaying senescence, reducing stature, increasing the number of stems, or increasing biomass in a plant, the method comprising: (i) introducing into the plant a construct comprising a plant promoter operably linked to a heterologous polynucleotide, the heterologous polynucleotide encoding a B3 domain protein comprising an amino acid sequence with at least 95% identity to SEQ ID NO:15, and (ii) selecting a plant exhibiting, relative to a plant lacking the construct, a phenotype selected from the group consisting of delayed senescence, shorter stature, increased number of stems, and increased biomass.

2. The method of claim 1, wherein the B3 domain protein comprises SEQ ID NO:15.

3. The method of claim 1, wherein the plant promoter is a constitutive promoter.

4. The method of claim 1, wherein the plant promoter is a tissue specific promoter.

5. The method of claim 4, wherein the plant promoter is a floral specific promoter.

6. The method of claim 4, wherein the plant promoter preferentially directs expression in ovules, pistils, anthers, fruits, seed coats, vascular tissues, provascular tissues, or apical meristems.

7. The method of claim 1, wherein the plant promoter is a senescence inducible promoter.

8. The method of claim 1, wherein the selecting step comprises selecting a plant exhibiting delayed senescence relative to a plant without the construct.

9. The method of claim 8, wherein the selecting step comprises selecting a plant with delayed senescence in a vegetative plant structure.

10. The method of claim 9, wherein the vegetative structure is a leaf, stem or root.

11. The method of claim 8, wherein the selecting step comprises selecting a plant with delayed senescence in a reproductive plant structure.

12. The method of claim 11, wherein the reproductive structure is a seed, embryo, ovule, flower, pistil, anther or fruit.

13. The method of claim 1, wherein the selecting step comprises selecting a plant with increased biomass relative to a plant without the construct.

14. The method of claim 8, wherein the selecting step comprises selecting a plant with delayed ovule senescence relative to a plant without the construct.

15. The method of claim 1, wherein the selecting step comprises selecting a plant with shorter stature relative to a plant without the construct.

16. The method of claim 1, wherein the construct is introduced by a sexual cross.

17. The method of claim 1, wherein the B3 domain protein comprises SEQ ID NO:12.

18. The method of claim 1, wherein the B3 domain protein comprises SEQ ID NO:14.

* * * * *